US008658750B2

(12) United States Patent
Lattner et al.

(10) Patent No.: US 8,658,750 B2
(45) Date of Patent: Feb. 25, 2014

(54) SYSTEM AND METHOD FOR SELECTIVE TRIMERIZATION

(75) Inventors: James R. Lattner, La Porte, TX (US);
Michael W. Weber, Houston, TX (US);
Jimmy L. Tardy, Crosby, TX (US);
Howard G. Large, La Porte, TX (US);
Peter N. Loezos, Houston, TX (US);
Randy L. Foster, Crosby, TX (US);
Jason D. Davis, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/577,449

(22) PCT Filed: Mar. 9, 2010

(86) PCT No.: PCT/US2010/026661
§ 371 (c)(1),
(2), (4) Date: Nov. 9, 2012

(87) PCT Pub. No.: WO2011/112184
PCT Pub. Date: Sep. 15, 2011

(65) Prior Publication Data
US 2013/0144024 A1    Jun. 6, 2013

(51) Int. Cl.
*C07C 7/10* (2006.01)
*C07C 2/30* (2006.01)
*C07C 2/02* (2006.01)
*C08F 110/02* (2006.01)
*C07C 2/26* (2006.01)
*C07C 7/00* (2006.01)
*B01J 21/00* (2006.01)

(52) U.S. Cl.
USPC ........... 526/352; 585/504; 585/511; 585/868; 502/100; 502/117

(58) Field of Classification Search
USPC .......... 526/352; 585/504, 511, 868; 502/100, 502/117
See application file for complete search history.

(56) References Cited

U.S. PATENT DOCUMENTS

| 3,300,458 A | 8/1963 | Manyik et al. |
| 4,472,525 A | 9/1984 | Singleton |
| 4,689,437 A | 8/1987 | Murray |
| 4,777,315 A | 10/1988 | Levine et al. |
| 5,376,612 A | 12/1994 | Reagen et al. |
| 5,451,645 A | 9/1995 | Reagen et al. |

(Continued)

FOREIGN PATENT DOCUMENTS

| WO | WO 2005-084772 | 9/2005 |
| WO | WO 2007-092217 | 8/2007 |

*Primary Examiner* — William Cheung
(74) *Attorney, Agent, or Firm* — Leandro Arechederra, III

(57) ABSTRACT

Disclosed herein is a method for separating from the reactor effluent of an olefin oligomerization procedure those catalyst materials and polymeric by-products which can cause difficulties in the downstream processing of such effluent. Polymer by-products and catalyst in the effluent are separated from reaction products by flash vaporization utilizing an in-situ hot solvent which is contacted with the effluent and serves as the heating medium to promote this flash vaporization step. Subsequent processing of a liquid portion of the effluent which is left after flash vaporization involves recovery of catalyst and polymeric by-products therefrom in a steam stripping vessel. Also disclosed is a multiple reactor system which can be used for continuous trimerization of ethylene to 1-hexene while at the same time washing polymeric by-products from one of the reactors in the series using a wash oil solvent.

20 Claims, 14 Drawing Sheets

(56) References Cited

U.S. PATENT DOCUMENTS

| | | |
|---|---|---|
| 5,557,026 A | 9/1996 | Tanaka et al. |
| 5,563,312 A | 10/1996 | Knudsen et al. |
| 5,668,249 A | 9/1997 | Baardman et al. |
| 5,689,028 A | 11/1997 | Lashier et al. |
| 5,731,487 A | 3/1998 | Tamura et al. |
| 5,763,723 A | 6/1998 | Reagen et al. |
| 5,814,575 A | 9/1998 | Reagen et al. |
| 5,853,551 A | 12/1998 | Boucot et al. |
| 5,856,610 A | 1/1999 | Tamura et al. |
| 5,859,303 A | 1/1999 | Lashier |
| 5,919,996 A | 7/1999 | Freeman et al. |
| 5,968,866 A | 10/1999 | Wu |
| 6,031,145 A | 2/2000 | Commereuc et al. |
| 6,265,513 B1 | 7/2001 | Murray et al. |
| 6,268,447 B1 | 7/2001 | Murray et al. |
| 6,277,841 B1 | 8/2001 | Rajagopalan et al. |
| 6,303,719 B1 | 10/2001 | Murray et al. |
| 6,320,002 B1 | 11/2001 | Murray et al. |
| 6,337,297 B1 | 1/2002 | Mimura et al. |
| 6,380,451 B1 | 4/2002 | Kreischer et al. |
| 6,455,648 B1 | 9/2002 | Freeman et al. |
| 6,521,806 B1 | 2/2003 | Tamura et al. |
| 6,583,083 B2 | 6/2003 | Murray et al. |
| 6,800,702 B2 | 10/2004 | Wass |
| 7,157,612 B2 | 1/2007 | Ewert et al. |
| 2007/0185358 A1 | 8/2007 | Buchanan et al. |
| 2007/0185364 A1* | 8/2007 | Buchanan et al. ............ 585/533 |
| 2008/0058486 A1 | 3/2008 | McCullough et al. |
| 2008/0182989 A1 | 7/2008 | Ackerman et al. |
| 2008/0188633 A1 | 8/2008 | Ackerman et al. |
| 2008/0200626 A1 | 8/2008 | Ackerman et al. |
| 2008/0200743 A1 | 8/2008 | Ackerman et al. |

\* cited by examiner

SYSTEM AND METHOD FOR SELECTIVE TRIMERIZATION

PRIORITY CLAIM

This application is a National Stage Application of International Application No. PCT/US2010/026661 filed Mar. 9, 2010, which is hereby incorporated by reference in its entirety.

FIELD OF THE INVENTION

The invention described herein relates to especially effective means and procedures for separating olefin products like 1-hexene, unreacted reactants such as ethylene and diluents from catalyst material and polymeric by-products found in a reactor effluent from an olefin oligomerization, e.g., trimerization, process. The invention described herein also relates to apparatus and processes for continuously oligomerizing, e.g., trimerizing, olefins such as ethylene to provide such oligomer-containing, e.g., 1-hexene-containing, reactor effluent without necessarily having to interrupt reactor effluent flow during reactor maintenance and cleaning to remove polymeric foulants.

BACKGROUND OF THE INVENTION

1-Hexene can be produced in high selectivity via ethylene trimerization using homogeneous, single-site chromium catalyst systems, activated by a molar excess of alkyl aluminums such as methyl alumoxane (MAO) and modified methyl alumoxane (MMAO). In an unavoidable side reaction, a small fraction of the converted ethylene forms polyethylene. This polyethylene polymer can take any or all of the following three forms: (i) it can coat surfaces of the reactor and associated piping; (ii) it can flow out of the reactor in solution with the reaction mixture; or (iii) it can flow out of the reactor as a suspended solid in the reaction mixture. In addition, the formation of polymer can continue downstream of the reaction system due to the presence in the reactor effluent of the still-active homogeneous catalyst.

A number of procedures have been developed for dealing with the problems of polymeric by-product formation and the presence of such polymeric by-product as well as active catalyst in ethylene trimerization reactor effluent. For example, U.S. Pat. No. 6,380,451 discloses a method for killing the catalyst after it leaves an ethylene trimerization reactor by contacting the reactor effluent with an alcohol. An excess of alcohol is required, with a 5:1 mole ratio of alcohol to total catalyst metals being preferred. The preferred alcohol is one with a high enough boiling point such that it can be easily separated from the desired hexene product by distillation. This '451 patent also discloses a method for cleaning the polymer and catalyst residues which deposit on the internal surfaces of the reactor. Polymer is removed by periodic washing with the reaction diluent at a temperature 60° C.-70° C. higher than the trimerization reaction temperature. In addition, this patent discloses cyclohexane as the preferred diluent/solvent in the reactor, as a good solvent is preferred to keep the catalyst system in solution.

U.S. Pat. No. 7,157,612 discloses another method for recovering polymeric by-products contained in the effluent of an ethylene trimerization reactor. Precipitation of by-product polymer within the reactor is minimized by operating the reactor temperature high enough to keep polymer in solution, with a preferred temperature being at least 110° C. Upon leaving the reactor, the effluent is contacted with an alcohol to deactivate the catalyst system. The effluent can then either be cooled, in which case some of the polymer precipitates and can be separated by filtration, or kept hot so that polymer stays in solution. In either case, soluble polymer continues to the downstream distillation columns where it is distilled away from the reaction products, diluents, and alcohol. In this manner, the polymer ends up with the catalyst and heavy by-product residues.

Some other trimerization catalyst systems have been developed which permit the ethylene trimerization reaction to be carried out with high selectivity. For example, U.S. Patent Application Publication Nos. 2008/0058486; 2008/0182989; 2008/0188633; 2008/0200626 and 2008/0200743 all disclose the use of catalyst systems which are soluble in light paraffins, such as $C_3$-$C_6$ iso- and normal paraffins, and which exhibit high activities and improved selectivities at very moderate temperatures of 60° C.-80° C. The use of such light solvents and mild reaction temperatures results in at least a portion, if not most or all, of the by-product polymer being formed as an insoluble precipitate. Some of the insoluble polymer precipitates on the surfaces within the reactor and in the outlet piping. The insoluble polymer which does not stick to these surfaces exits the reactor as a suspended solid.

Prior art methods for dealing with the presence of active catalyst and polymer by-products in the trimerization reactor effluent have encountered some problems. For example, the Cr-based trimerization catalysts typically employ an excess of aluminum alkyl activator relative to Cr compounds. In some systems, this excess can be 100:1 molar equivalents of Al to Cr or more, up to 1000:1. The alcohols used to deactivate the catalyst are not selective to the Cr compounds since the alcohol also reacts with the Al compounds. An excess of alcohol over both Cr and Al is therefore required to ensure all active Cr species have reacted. The '451 and '612 patents discussed above, for example, teach use of a 5:1 molar excess of alcohol to total metals. If the Al:Cr ratio is 200:1 and a molar excess of alcohol to total metals of 5:1 is employed, then the molar excess of alcohol to Cr compound is 1000:1. This exceedingly high excess requirement for alcohol is costly, and also requires the addition of a distillation column for recovery of the unreacted alcohol for efficient utilization of the alcohol.

Prior art methods for separating polymer by-product from the reactor effluent can also be cumbersome. Not all of the polymer contained in the reactor effluent can be separated by filtration, even if the effluent is cooled. Some of the polymer is still in solution, which carries through to the distillation columns. As the polymer is concentrated through successive distillation steps to recover reactants, products, and diluents, the polymer can precipitate and foul the column internals and reboilers.

Finally, build-up of polymeric by-product which remains within the oligomerization reactor itself and in associated reactor piping can be troublesome. After polymer by-products like polyethylene have fouled internal reactor surfaces and piping, it may become necessary to shut down the reactor(s) and wash the reactor(s) and piping out with a suitable solvent or wash liquid which can remove the built-up by-products. Shutting down of the reactor(s) for cleaning and maintenance is, of course, economically disadvantageous because production of the desired oligomerization product is interrupted.

In view of the foregoing difficulties which can arise in dealing with catalyst and polymeric by-products found in the reactor effluent from olefin oligomerization processes, it would be advantageous to provide procedures and apparatus configurations for efficiently and cost-effectively treating such reactor effluent to separate catalyst material and polymeric by-products from the rest of the effluent components. Further in view of the difficulties which can arise as a result of polymeric by-product build-up in the reactors themselves, it would be advantageous to provide apparatus and process arrangements which eliminate or minimize the need for complete olefin oligomerization shutdown during reactor maintenance and cleaning. Such procedures, apparatus configurations and processes are embodied in the separation and cleaning techniques and apparatus configurations described herein.

SUMMARY OF THE INVENTION

The present invention relates to a process for oligomerizing ethylene to alpha-olefin product comprising the steps of:
A) oligomerizing ethylene in a diluent using a catalyst to produce a liquid reactor effluent comprising alpha-olefin product, polymeric by-product, catalyst material, and reaction diluent;
B) contacting said reactor effluent with a solvent at pressure and temperature conditions suitable to vaporize a major portion of said alpha-olefin product but not suitable to vaporize a major portion of said polymeric by-product and said catalyst material to form a combined solvent effluent;
C) separating said combined solvent effluent into a vapor phase comprising a major portion of said alpha-olefin product and a liquid phase comprising a major portion of said polymeric by-products and said catalyst material and a major portion of said solvent;
D) recirculating a first portion of said liquid phase and contacting the reactor effluent as set forth in Step B; and
E) purging a second portion of said liquid phase in order to remove polymeric by-products and catalyst from said process.

DETAILED DESCRIPTION OF THE INVENTION

Figure 1:
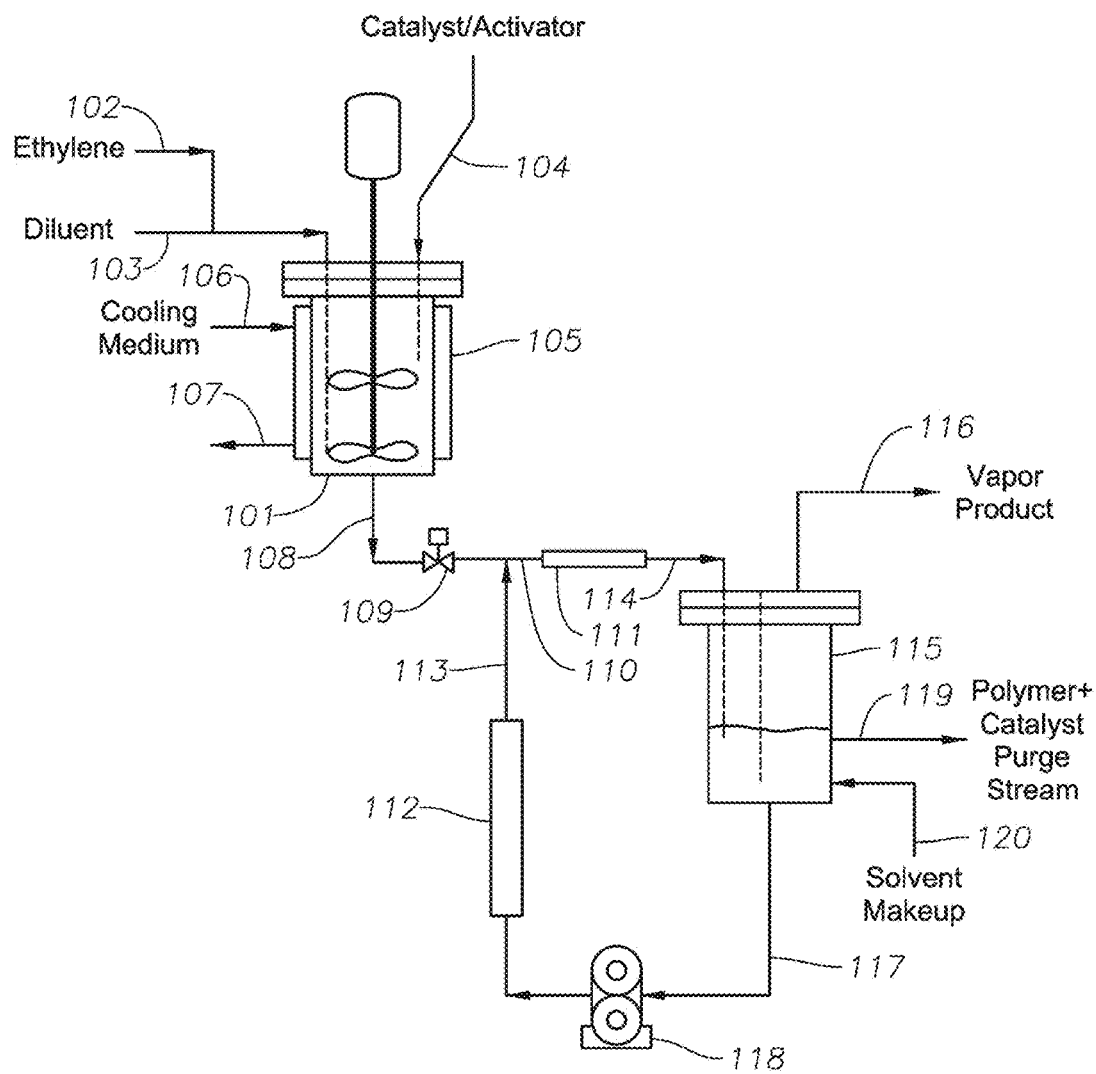
FIG. 1 illustrates the flash vaporization procedure and apparatus used to separate the components of effluent from an olefin oligomerization reactor.

In the principal effluent treatment method disclosed herein, catalyst material, unreacted ethylene, and polymeric by-products are separated from 1-hexene and reaction diluent in the reactor effluent formed from a continuous process for selectively trimerizing ethylene to 1-hexene. This is accomplished by flash vaporization of the effluent utilizing in-situ contact of the effluent with a hot solvent as the heating means and medium. This provides an effective way for separating the by-product polymer from the 1-hexene product, as well as for separating reactive species from the catalyst, thereby preventing undesirable further reactions in the downstream equipment.

Catalytic trimerization of ethylene to selectively produce 1-hexene is a well known reaction and process. Reactants, catalysts, diluents, reaction conditions and reactor and separation apparatus configurations for such processes of this type are disclosed, for example; in U.S. Pat. Nos. 6,380,451 and 7,157,612 and in U.S. Patent Application Publication Nos. 2008/0058486; 2008/0182989; 2008/0188633; 2008/0200626; and 2008/02007413. All of these patent documents are incorporated herein by reference in their entirety.

In the methods disclosed herein, the principal reactant ethylene can be selectively trimerized to produce 1-hexene. Other olefin reactants such as propylene, 1-butene, and 2-butene and the like; may also be trimerized as part of the reactor feed. Ethylene and/or the other olefins can also be dimerized or tetramerized as part of the reaction carried out in connection with the method herein.

Catalysts used to promote olefin, e.g., ethylene, oligomerizaton, e.g., trimerization, will generally comprise homogeneous, organometallic systems, for example, single site chromium catalyst systems. Such systems can comprise a chromium source in combination with a heterocyclic, di-aryl or phosphorus compound such as a pyrrole, pyridyl or pyridyl-phosphino compound, along with an alkyl aluminum activator such as methyl alumoxane (MAO) or modified methyl alumoxane (MMAO).

The olefin reactant(s) will generally be fed to the oligomerization reactor along is with a suitable diluent. For purposes of this description, a "diluent" will be defined as the material added to the reactor feed, in addition to the ethylene or other olefin "reactant". The diluents used herein will generally have a boiling point of from about 50° C. to 120° C. or higher. Such a diluent can typically be an inert hydrocarbon, such as $C_3$-$C_6$ normal and iso-paraffins, but can also be a cycloparaffin or aromatic compound. Olefins themselves can also be used as the reaction diluent. Olefins, however, are not preferred since, as noted, they can also serve as a reactant, depending on the catalyst system and conditions employed. As used herein, the term "diluent" is distinct from the term "solvent" which, as hereinafter noted, is reserved for the material(s) used as the heat transfer media for conducting the flash vaporization of the reactants, products, and diluents.

Conditions of temperature, pressure, flow rates and residence times in the oligomerization, trimerization, reactor are conventional and well known. Temperature in the reactor can range from about 25° C. to 100° C., more preferably from about 50° C. to 90° C. External cooling of the reactor may be needed to maintain such reactor temperature conditions within the desired range.

Pressure in the reactor can generally range from about 0 psig kPa) to 1200 psig (8273 kPa), more preferably from about 200 psig (1379 kPa) to 800 psig (5516 kPa). The effluent from the reactor will generally comprise the desired products(s), e.g., 1-hexene; unreacted reactant(s), e.g., ethylene; polymeric by-products, e.g., polyethylene; catalyst; and diluent. This effluent leaving the reactor will generally be under temperature and pressure conditions essentially the same as those found within the reactor.

After leaving the reactor system, the pressure of the effluent stream is reduced, and the effluent is then contacted with a stream of heated solvent. Reduction of effluent pressure and the heating of the effluent stream by combining it with hot solvent both serve to effect rapid separation of the combined effluent/solvent stream into vapor and liquid phases when this combined stream is subsequently introduced into a flash separator. After pressure reduction, the pressure of the effluent stream; as well as pressure conditions in the flash separator, should be in the range of from about 0 psig (0 kPa) to 200 psig (1379 kPa), more preferably from about 50 psig), (345 kPa) to 150 psig (1034 kPa).

While referred to herein as a "solvent", the primary function of the heated liquid which is contacted with the reactor effluent stream is as a heat transfer fluid. This "solvent" therefore need not actually dissolve anything or exhibit good solvent properties. The most important characteristic of the solvent is that it have a high enough boiling point to have a major portion thereof be maintained in the liquid phase in the flash separator. Further, the boiling point of the solvent should also be high enough so that any solvent which is vaporized in the flash separator is easy to separate from the product hexene by distillation.

As used herein, "major portion" means at least about 50 wt %, or at least about 75 wt %, or at least about 90 wt %, or at least about 95 wt %, or at least about 98 wt %, or at least about 99 wt %, based upon total weight of the stream. "Minor portion" means less than about 50 wt %, or less than about 40 wt %, or less than about 30 wt %, or less than about 20 wt %, or less than about 10 wt %, or less than about 5 wt %, or less than about 1 wt %, based upon total weight of the stream. These definitions apply to all components (solvent, etc.) and streams (e.g., vapor and liquid streams, etc.)

Given the foregoing, the solvent used in the method herein will generally have a boiling point of from about 100° C. to 220° C. Preferably, the boiling point of the solvent will be higher, e.g., at least 50° C. higher, than the boiling point of the reaction diluent. The solvent will generally also be inert, that is, not undergo reactions in the presence of the catalyst. Materials which exhibit the required properties for the solvent used herein include $C_8$+ normal and iso-paraffins, $C_7$+ cycloparaffins, and $C_6$+ aromatics. High boiling olefinic byproducts ($C_8$ and heavier) from the reaction step are also inevitably present in the reactor effluent and indeed can make up part of the "solvent". In fact, it is possible that the entire "solvent" consist of material that was produced in the reaction step, in particular $C_8$ and $C_{10}$ olefins and/or the hydrogenated reaction products thereof.

Prior to contact with the reactor effluent stream, the solvent will generally be heated to a temperature above that of the effluent stream exiting the reactor. Preferably also, the solvent will be heated to a temperature above the melting point of the polymer byproduct. Typically, the temperature of the solvent stream just prior to contact with the reactor effluent will range from about 120° C. to 300° C., more preferably from about 130° C. to 200° C. After solvent is combined with the effluent stream, the temperature of the combined effluent/solvent stream, and the temperature in the flash separator, will generally range from about 100° C. to 200° C.

Contact of the heated solvent with the reduced pressure effluent stream from the reactor is carried out in such a manner as to rapidly heat the effluent stream in-situ prior to combined stream being introduced into the flash separator. After the contacting is allowed to take place, the vapor and liquid streams are separated in the flash separator. If a light-boiling diluent is used in the reaction (such as $C_3$-$C_6$ normal and iso paraffins or olefins), a major portion of this diluent will also flash vaporize.

The vapor product from the flash separator, comprising the unreacted ethylene, hexene product, other olefin byproducts, at least a major portion of the diluent, and possibly a small amount of the solvent, will generally be fed to a series of distillation columns for recovery of the unreacted ethylene, diluent, hexene product, and solvent, as illustrated in several of the figures of drawings provided herewith. The by-product polymer and catalyst components of the stream introduced into the flash separator are not volatile and are practically absent in the vapor stream from the separator.

The liquid stream from the separator comprises the at least a major portion of the solvent, catalyst components, and polymer by-product. A small concentration of olefin products may also be present in the liquid stream, depending on the conditions of pressure, temperature, and the type of diluents and solvents employed.

From the foregoing it can be seen that by the principal method described herein, the problem of the presence of active catalyst and polymer by-product in the reactor effluent can be effectively dealt with simultaneously in a single process step. An interesting feature of this method is that the catalyst in the reactor effluent is not necessarily "killed" by the flash vaporization step. Instead, the reactive species (ethylene, and to a lesser extent, hexene) are quickly separated from the catalyst, such that the catalyst has no reactants to catalyze. This feature avoids the need to add excess amounts of an external kill agent, such as alcohol, thus avoiding the need to recover and recycle the unreacted catalyst kill agent in the downstream distillation process.

A first portion, i.e., a major portion, of the liquid phase from the flash separator is re-used as the heat transfer medium to effect additional flash vaporization. This first liquid portion can be recirculated to the reactor effluent stream with a pump through a heat exchanger, where the necessary heat duty for heating and vaporizing the effluent stream components is added. A high circulation rate of liquid relative to the reactor effluent is used to achieve rapid heat transfer to the reactor effluent, and to avoid the need for excessive temperatures in the heater.

A second, and minor, portion of the liquid phase from the flash separator must be purged, either continuously or periodically, to prevent continuous buildup of polymer by-product and catalyst components in the flash separator and the circulating solvent. The concentration of polymer and catalyst species in the purge stream can be controlled by adjusting the rate or frequency of purging. It is desirable to allow the concentration of polymer in the purge stream to build to high levels to make disposal or treatment of the purge stream easier. The upper concentration level will be limited by factors that include maintaining pumpability of the circulating solvent and purge streams.

In the principal method herein, it should be noted that the suitable temperatures and pressures for the flash vaporization step are inter-related. That is, a higher pressure in the flash separator will require a higher temperature to achieve good separation of the reactants and products into the vapor phase. Likewise, a lower pressure in the flash separator does not require the temperature therein to be so high. It has been found that a flash temperature (the temperature after mixing the hot solvent with the reactor effluent) of about 150° C. or higher is effective at flash separator pressures of about 80 psig (552 kPa).

It should also be noted that the circulation rate of the solvent is a useful variable for controlling the flash separation step of the method herein. The degree of circulation can be established by comparing the temperature of the flash at steady state with the temperature of the solvent leaving the recirculating solvent heater. The higher the ratio of circulating solvent flow to the reactor effluent flow, the lower the difference in these two temperatures will be (at steady state). It has been found that a temperature difference between the temperature of the recirculating solvent at the heater outlet and the flash temperature of from about 13° C. to 17 e.g., about 15 provides an adequate circulation rate ratio of solvent to effluent.

An apparatus arrangement/process flow diagram suitable for carrying out the principal separation method of this invention is provided by FIG. 1 of the drawings. In FIG. 1, an olefin reactant such as ethylene and a reaction diluent are fed to a Stirred Reactor 101 via feed lines, 102 and 103, respectively. The components of the catalyst system such as catalyst and activator material are also fed to the Stirred Reactor 101 via line 104. The Stirred Reactor 101 is fitted with a cooling jacket 105. Cooling medium is fed into the culling jacket via line 106, and out of the cooling jacket via line 107.

Reactor effluent containing, for example, 1-hexene product, unreacted ethylene, diluent, catalyst system material and one or more polymeric by-products, leaves the Stirred Reactor 101 via line 108 and is passed through a Pressure Reduction Valve 109 and via line 110 on to an optional Heat Transfer Contact Zone 111. In line 110 immediately before reaching the optional Heat Transfer Contact Zone 111, the reactor effluent is combined with recirculating heat transfer solvent coming from Heater 112 via line 113. Contact of reactor effluent and the heated recirculating heat transfer solvent, plus any additional heat added in the optional Heat Transfer Contact Zone 111, raises the temperature of the combined effluent/solvent stream which is then fed via line 114 to a Flash Separator 115.

In the Flash Separator 115, the combined effluent/solvent stream separates into a vapor phase and a liquid phase. Vapor Product, which comprises substantially all of the 1-hexene reaction product and unreacted ethylene, along with a major portion of the reaction diluent and a minor portion of the heat transfer solvent, is removed from the Flash Separator 115 via line 116 for separation into its component streams via distillation equipment (not shown in FIG. 1).

The liquid phase formed in the Flash Separator 115 comprises substantially all of the polymeric by-products and the catalyst material from the reactor effluent, along with some reaction diluent and a major portion of the heat transfer solvent. A first portion of this liquid phase is removed from the Flash Separator 115 via line 117 and fed via a Pump 118 to the Heater 112 as the recirculating heat transfer medium. A second minor portion of the liquid phase is continuously or intermittently removed from the Flash Separator 115 as a Polymer+Catalyst Purge Stream via line 119, and this Polymer+Catalyst Purge Stream conveyed via line 119 can be separated into its components via equipment not shown in FIG. 1 but described in subsequent figures hereinafter. To make up for heat transfer solvent removed from the Flash Separator 115 via the Polymer+Catalyst Purge Stream through line 119, fresh heat transfer solvent can be introduced into the Flash Separator 115 as Solvent Makeup via line 120.

In another embodiment, there is provided an additional separation method to separate and recover catalyst, polymeric by-products, reaction diluent and heat transfer solvent components from the processed effluent stream coming from a reactor wherein the catalytic trimerization of ethylene to 1-hexene has taken place. Such an additional separation method can involve treatment of the liquid portion of the flash vaporized effluent stream which is formed in a flash separator into which the oligomerization reactor effluent, along with added heat transfer solvent, has been fed. As described hereinbefore, this liquid portion which is to be separated into its components can comprise the purge stream taken continuously or intermittently from the flash separator. This purge stream represents that fraction of the liquid formed in the flash separator which is not recycled as a heat transfer solvent to contact the reactor effluent.

In connection with this additional separation method, the purge stream is sent, either continuously or periodically, to a steam-stripping vessel containing both water and steam. Steam is sparged into the stripping vessel below the level of liquid therein. Some of the steam condenses to heat the water in the vessel as well as the purge stream liquid being introduced. The remainder of the steam rises to the liquid surface, is separated from the liquid, and exits the stripping vessel as an overhead vapor stream.

The heating and dilution action of the steam vaporizes solvent and any reaction diluent from the purge stream, such that solvent and diluent are carried out of the vessel with the vapor stream. The intense mixing created by the steam sparger results in the effective contacting of the polymer by-product, catalyst metal species and solvent/diluent with the hot water and steam. This effective contacting is important to vaporize the solvent and diluent, as well as to effectively contact the catalyst metal species with water and steam. To further intensify the contacting, mechanical agitation of the steam stripper contents may optionally be utilized as well.

The catalyst metal species undergo rapid reaction with water to produce "inert" metal compounds, such as metal hydroxides. While the exact form of the metals (e.g., Al and Cr) from the catalyst after the flash vaporization of the reactor effluent is not known due to the heat treatment received, it is known that these metals are reactive with oxygen or moisture in the atmosphere. Accordingly, passivation is necessary prior to removing such components from the closed process system. In the present additional separation method, this passivation occurs in the steam stripping vessel.

The temperature of the steam stripping step will be dictated primarily by the pressure maintained on the stripping vessel. The pressure and temperature will roughly correspond with the vapor pressure and temperature of pure water/steam systems. It is desirable to maintain a temperature as high as possible, but below the melting point of polyethylene, which is about 120° C. Avoiding molten polymer in the stripping vessel makes removal of polymer from the water phase much easier, since molten polymer tends to stick to itself and to surfaces. Atmospheric pressure, or just above atmospheric, is a good choice for pressure, so that the temperature of the boiling water is 100° C.-110° C. This is hot enough to strip solvent and diluent with steam, but below the melting point of polymer to make a less sticky polymer by-product. Vacuum can also be used for the stripping step, by the addition of a vacuum pump or ejector system to maintain the vacuum. Vacuum operation results in a lower temperature of the boiling water mixture. This can allow operation further from the melting point of the polymer, thereby rendering the polymeric material less sticky.

The polymer by-product can be removed from the stripping vessel, either batch-wise, continuously, or periodically. It is desirable to add the solvent purge stream to the stripping vessel such that small "crumbs" of polymer are formed, as these are easier to remove in a continuous or periodic fashion. The addition of solvent-containing purge stream too quickly tends to form large "chunks" of polymer, which are more difficult to remove from the vessel. Typically this requires that the vessel be shut down, cooled, and opened for cleaning out the polymer by-product material.

Other methods may be employed to ensure that the polymer precipitates as small particles, and not form large agglomerates that are difficult to remove from the steam stripping vessel. One method is to inject the feed solvent/polymer mixture into the stripping vessel under conditions of high shear. The high shear can be achieved from a high velocity nozzle, high velocity steam co-injection, mechanical agitation, or any combination thereof Another method is to add a surface-active material to the stripping vessel to reduce the tendency of the polymer particles to stick together.

An advantage of the additional separation method described herein is that the catalyst kill/passivation agent, water, can be contacted with the active catalyst metals in a relatively small purge stream, and not on the bulk reactor effluent. If water were to be used to kill the catalyst in the bulk reactor effluent stream, at least some of this water would end up in the unreacted ethylene and diluent stream that is recycled to the reactor. This would result in severe deactivation of the catalyst in the oligomerization reaction process. In the present additional separation method, the water contacting preferably occurs on a small purge stream. While it may be desirable to recycle the solvent recovered from the steam stripping step, it is relatively simple to remove water from the small solvent recycle stream, compared with the large ethylene/diluent recycle stream.

In another embodiment of the additional separation method, the pH of the water in the stripping vessel can be adjusted to cause the passivated metals to convert to a desirable form. In some cases, it may be desirable for one or more of the metals to precipitate in the stripping vessel, in which case the metals exit with the precipitated polymer by-product. In other cases, it may be desirable for one or more of the metals to be soluble in the water, in which case the metals exit with a water blowdown stream for treatment in a wastewater plant (or even for possible metals recovery). The pH of the water is adjusted by the addition of an acid or a base. Selection of the acid or base is not critical for the metal chemistry, but is typically based on the cost to purchase the material, as well as for waste water treatment cost or environmental factors.

In yet another embodiment of the additional separation method, specification of the properties of the "solvent" is narrowed further to enhance the ability to remove solvent from the polymer by-products. Since, as noted hereinbefore, the purpose of the "solvent" is to serve as a heat transfer fluid, and not to necessarily "dissolve" polymer, selection of a fluid that is actually a poor solvent for the polymer can be useful. Examples of "poor" solvents are $C_8$-$C_{12}$ iso and normal paraffins and olefins. Lighter boiling solvents are not preferred because they are difficult to separate from the hexene product. Heavier solvents are not preferred because they are difficult to remove from the by-product polymer.

It has been observed that the use of solvents such as "Isopar G" or "Isopar H" marketed by ExxonMobil Chemical result in a cloudy appearance of the liquid generated in the flash vaporization step of the principal separation method herein for product recovery. This means that at least some of the polymer is not in solution, but rather in a fluid suspension within the solvent. Upon cooling of a polymer-containing "solvent" stream, additional polymer precipitates. Upon settling, the "polymer-rich" phase settles to the bottom, and a clear liquid layer appears on top.

Such a settling step can be used before the steam stripping step to concentrate polymer in the liquid before stripping, reducing the amount of solvent that must be stripped from the polymer. The catalyst metals passivation step is relatively fast while the solvent removal step is relatively slow. Therefore, increasing the concentration of polymer before the stripping step reduces the amount of time and steam required to remove solvent from the polymer by-product. When a settling step is used, the upper liquid layer ("polymer-lean" liquid) can be recycled throughout a pump to the flash vaporization vessel used for the heated reactor effluent. While the upper liquid layer will not be free of dissolved polymer or catalyst components, one skilled in the art will recognize that the system can be operated at a steady state, such that the rate of purging of polymer by-product and catalyst components in the polymer-rich phase will equal the production rate.

As mentioned, the "solvent" may comprise components that are produced as by-products in the oligomerization reaction step. Such by-products, typically $C_8$, $C_{10}$ and $C_{12}$ linear and straight-chain molecules, are mostly olefinic in nature. Because of their olefinic nature, they are not truly inert, that is, they may undergo additional reactions in the presence of the un-passivated catalyst metals species. In yet another embodiment of both the principal and additional separation methods herein, at least a portion of the olefinic by-products in the reactor effluent can be hydrogenated to saturate these olefins, forming normal and iso-paraffins. These hydrogenated by-products can then be recycled to serve as inert solvent for the flash vaporization step of the principal separation method herein.

In the additional separation method herein, the overhead vapor stream leaving the steam stripping vessel mainly comprises water and solvent vapors. Upon cooling, the water and solvent can be condensed at temperatures above ambient. Most of the water is easily separated from the solvent by settling and decanting. The oil layer, however, will still be saturated with dissolved water. It is important to remove this water before returning the solvent to the flash vaporization step of the principal separation method herein. If wet solvent were returned there, some of the water would flash and recycle to the reactor with the ethylene and/or reaction diluent.

One method of removing water from the solvent recycle is to pass the water-containing solvent over a bed of desiccant. This requires at least one additional vessel for the desiccant, plus either a regeneration system or periodic replacement of the desiccant with fresh material. In another embodiment of the additional separation method herein, the recycle solvent can be dried by distillation, utilizing a column already present in the process. In this manner, no additional vessels, desiccant replacement, or regeneration systems are required.

Figure 2:
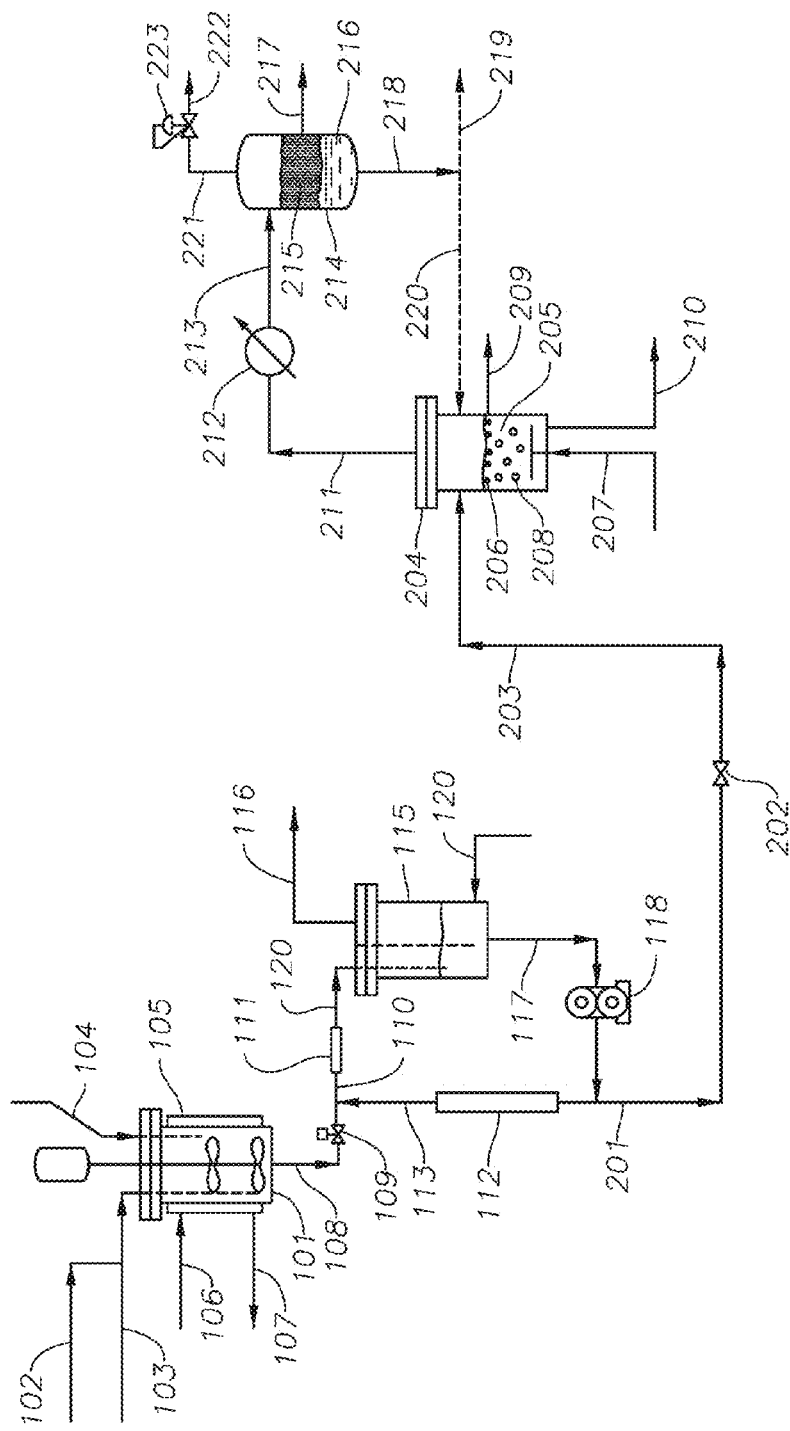
FIG. 2 illustrates further treatment of a liquid fraction obtained by the flash vaporization of the olefin oligomerization reactor effluent.

An apparatus arrangement/process flow diagram suitable for carrying out the both the principal separation method and the additional (or further) separation method of this development is provided by FIG. 2 of the drawings. In FIG. 2, the Reactor 101, the Flash Separator 115, the Vapor Product transfer line 116, the Solvent Makeup introduction line 120, the recycle Pump 118, the recycle solvent Heater 112, and the optional Heat Transfer Contact Zone ill are the same as those elements which are described in FIG. 1 hereinbefore. In FIG. 2, the polymer+Catalyst Purge Stream shown in FIG. 1 as being removed from the Flash Separator 115 via line 119 is replaced with a Polymer+Catalyst Purge Stream transfer line 201 branching off from the recycle Pump 118 instead. The Polymer+Catalyst Purge Stream from the solvent recycle Pump 118 is conducted via this line 201 through Purge Control Valve 202 and through line 203 into Stripping Vessel 204.

Stripping Vessel 204 contains a liquid layer 205 comprising water and liquid components (e.g., solvent and diluent) from the Polymer+Catalyst Purge Stream. Within the liquid layer 205, there are solid Polymer Particles 206 and possibly also solid catalyst metal compounds, not shown, as well. Steam is introduced into the Stripping Vessel 204 via line 207, and this steam introduction creates Steam Bubbles 208 in the liquid layer 205. Steam bubbling through the liquid layer 205 serves to passivate the metal catalyst compounds which have been introduced into the liquid layer 205 in the Stripping Vessel 204 via the Polymer+Catalyst Purge Stream.

By-Product Polymer material along with some passivated catalyst metal compounds (if solid) are separated from the liquid layer 205 and removed from the Stripping Vessel 204 via line 209. Water can be removed from the Stripping Vessel 204 as Water Blowdown via line 210. Some passivated water-soluble catalyst metal compounds are also removed from the Stripping Vessel 204 via this Water Blowdown stream through line 210.

Steam and components in the liquid layer 205 such as solvent and reaction diluent which have been volatilized by steam are vented as an overhead vapor stream from the top of the Stripping Vessel 204 via line 211. This overhead vapor stream is condensed in Condenser 212 with the resulting condensed liquid stream fed via line 213 to Separator 214. In the Separator 214, the condensed liquid separates into an oil layer 215 and a water layer 216. Solvent can be recovered from the oil layer 215 via line 217. Water can be withdrawn from the water layer 216 via line 218 and either purged via line 219 and/or optionally returned to the Stripping Vessel 204 via line 220. Overhead vapor can be vented, for instance to a flare, via lines 221 and 222 and Pressure Controller 223.

Figure 3:
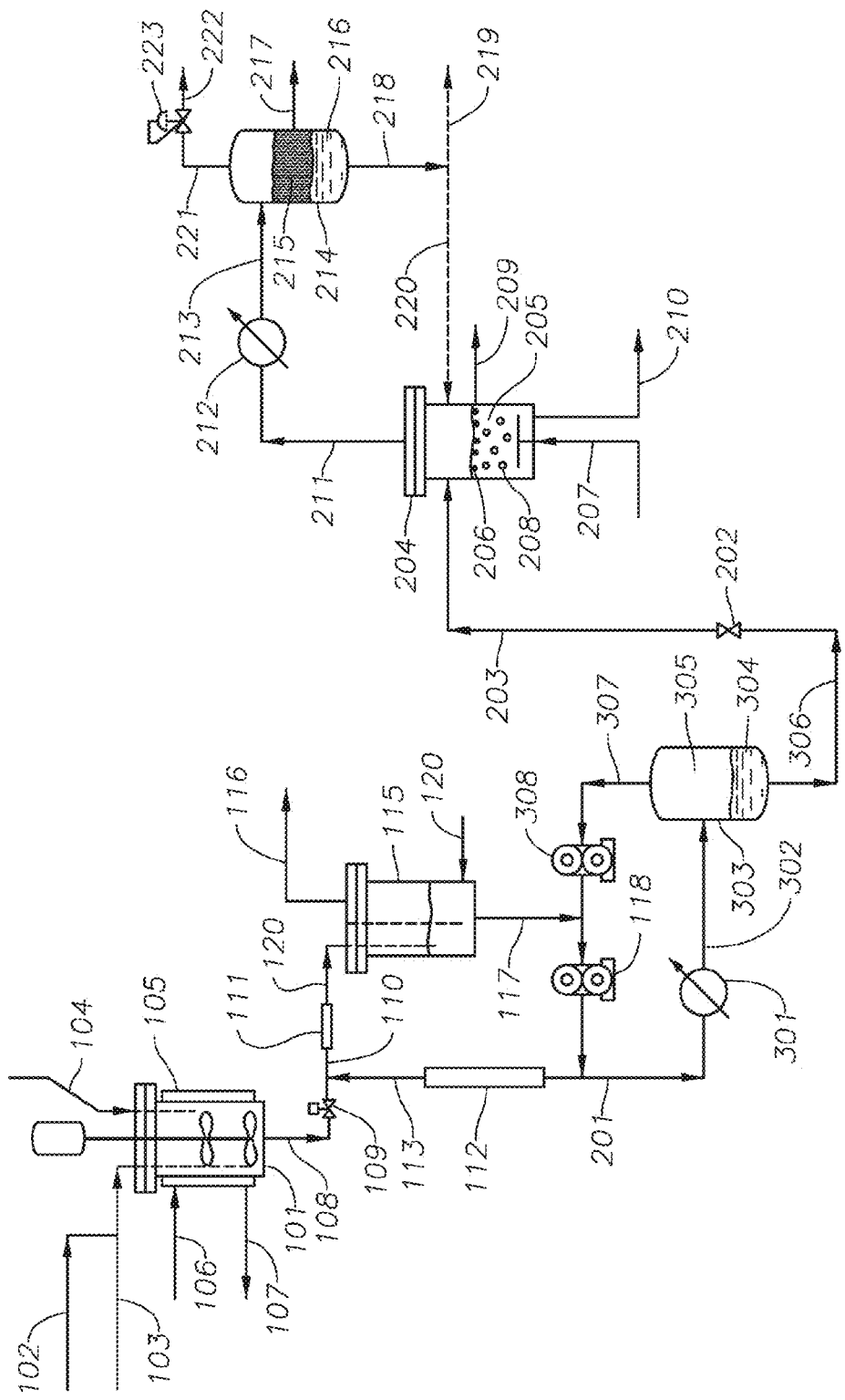
FIG. 3 illustrates still further treatment of a liquid fraction obtained by the flash vaporization of the olefin oligomerization reactor effluent.

An apparatus arrangement/process flow diagram suitable for carrying out both the principal separation method and another embodiment of the additional (or further) separation method of this development is provided by FIG. 3 of the drawings. In FIG. 3, the reactor and flash separation arrangement is same as shown in FIGS. 1 and 2 with Elements 101, 111, 112, 115, 116, 118, and 120 thereof being the same as described hereinbefore in FIGS. 1 and 2. Further in FIG. 3, the solvent/by-product polymer/catalyst recovery arrangement is the same as depicted in FIG. 2 with Elements 201 to 223 thereof being the same as described hereinbefore in FIG. 2, FIG. 3 depicts the positioning of a cooling/polymer-settling operation between the reactor/flash separation arrangement and the solvent/by-product polymer/catalyst recovery arrangement.

In FIG. 3, the Polymer+Catalyst Purge Stream from the flash separation arrangement is fed via line 201 to a Cooler 301 and then via line 302 to a Polymer Settling Vessel 303. In the Polymer Settling Vessel 303, more of the by-product polymer precipitates from the cooled Polymer+Catalyst Purge Stream and settles toward the bottom of the liquid in the Polymer Settling Vessel 303. This provides a polymer-rich liquid phase 304 toward the bottom of the Polymer Settling Vessel 303 and a polymer-lean liquid phase 305 toward the top of the Polymer Settling Vessel 303.

The polymer-rich liquid phase 304 can be taken from the bottom of the Polymer Settling Vessel 303 and fed via line 306 to the Purge Control Valve 202 and then on for processing in the solvent/by-product polymer/catalyst recovery arrangement. The polymer-lean liquid phase 305 can be taken from the top of the Polymer Settling Vessel 303 and fed via line 307 through an Optional Pump 308 hack to the recirculating solvent/flash vaporization operation. Use of this cooling/polymer settling system permits more efficient recovery of by-product polymer in the subsequent steam stripping operation and more efficient operation of the heat transfer solvent recirculation operation to drive the flash separation step of the principal separation method herein.

Figure 4:
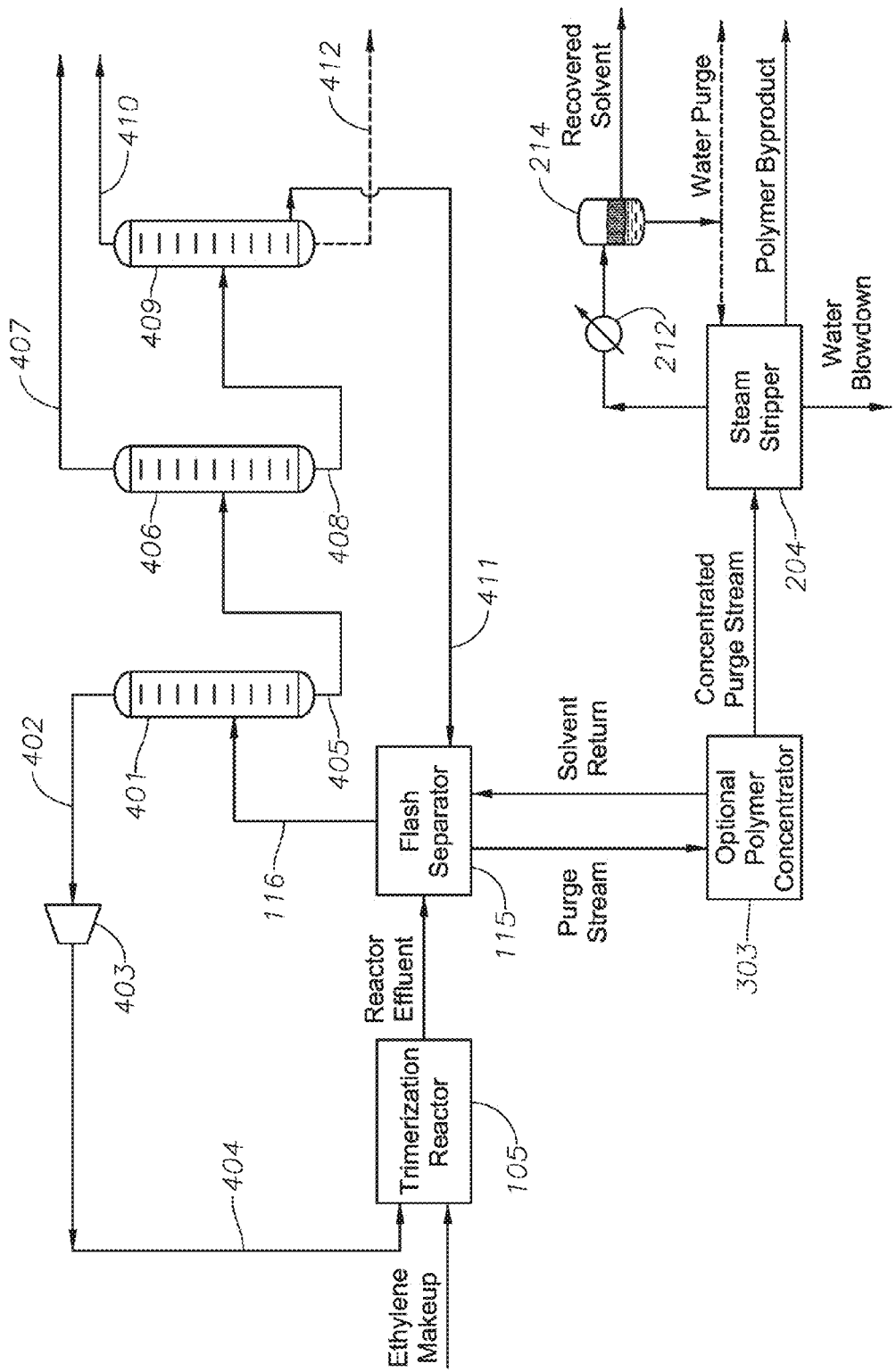
FIG. 4 illustrates treatment of both the vapor fraction and liquid fraction obtained by the flash vaporization of the olefin oligomerization reactor effluent.

FIG. 4 of the drawings depicts an apparatus arrangement/process flow diagram suitable for recovering from the flash separator overhead vapor product the following materials: oligomerization product (e.g., hexene), oligomerization by-products (e.g., $C_8$-$C_{10}$ olefins), unreacted oligomerization reactant (e.g., ethylene), reaction diluent and heat transfer solvent. In FIG. 4, the Trimerization Reactor 105, the Flash Separator 115, an Optional Polymer Concentrator (Settling Vessel) 303 and Steam Stripper 204 with its associated condenser 212 and Separator 214 are the same as these elements are described in the several preceding figures of the drawings.

In FIG. 4, the overhead Flash Vapor from the Flash Separator 115 is fed via line 116 to a Recycle Column 401. In Recycle Column 401, ethylene and reaction diluent from the Flash Vapor are separated as overhead from the heavier components of the Flash Vapor. This separated ethylene and reaction diluent are sent via line 402 to compressor 403 and then via line 404 as recycle to the Trimerization Reactor 105.

Bottoms from the Recycle Column 401 are fed via line 405 to a Hexene Column 406. In Hexene Column 406, the hexene product is separated from heavier components, including heat transfer solvent, and is removed as overhead from the Hexene Column 406 via line 407. Bottoms from the Hexene Column 406 are removed via line 408 and fed to a $C_8$-$C_{10}$ Column 409. In the $C_8$-$C_{10}$ Column 409, the $C_8$-$C_{10}$ Olefin By-Products are separated from bottoms comprising heat transfer solvent and other heavies and removed from the $C_8$-$C_{10}$ Column 409 via line 410.

Heat transfer solvent is removed from the bottom of the $C_5$-$C_{10}$ Column 409 and fed via line 411 as Solvent Recycle to the Flash Separator 115. Other heavier products can be removed from the $C_8$-$C_{10}$ Column 409 via line 412 as an Optional Heavies Purge Stream.

Figure 5:
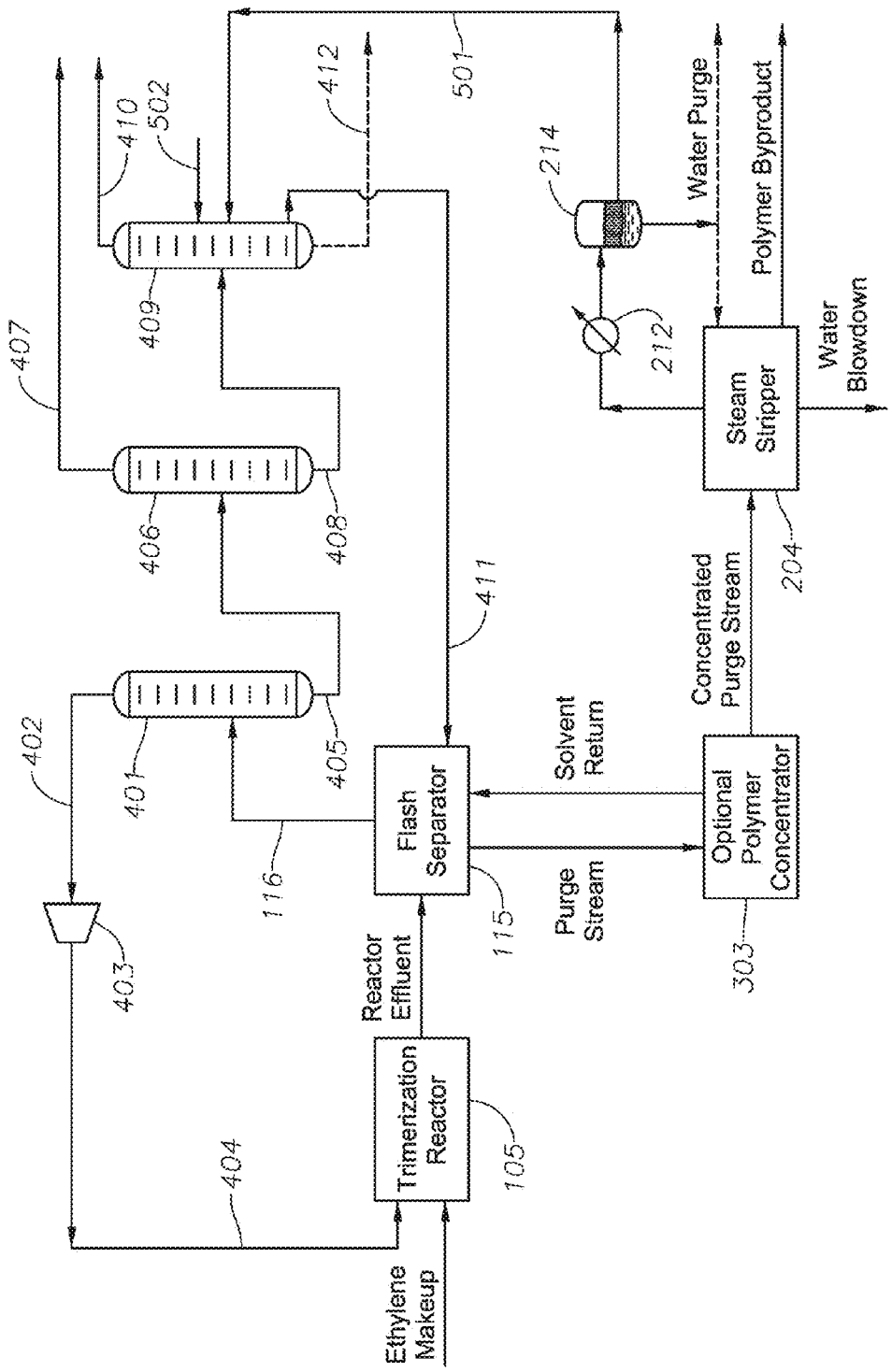
FIG. 5 illustrates solvent recovery from the treatment of both the vapor fraction and liquid fraction obtained by the flash vaporization of the olefin oligomerization reactor effluent.

FIG. 5 of the drawings shows how the same apparatus and similar flow arrangement of FIG. 4 can be used to dry heat transfer solvent recovered from the steam stripping operation and recycle that dried heat transfer solvent back to the flash separation operation. In FIG. 5, wherein all of the same elements as in FIG. 4 are shown, water-containing solvent recovered from the Separator 214 associated with the Steam Stripper 204 is fed via line 501 to the $C_8$-$C_{10}$ Column 409.

In the $C_8$-$C_{10}$ Column 409, water dissolved in the solvent recovered from the Separator 214 is separated from the solvent and vented from the $C_8$-$C_{10}$ Column 409 as overhead along with the $C_8$-$C_{10}$ Olefin By-Products through line 410.

Solvent from the bottom of the $C_8$-$C_{10}$ Column 409, which now includes dried solvent recovered from the Separator 214, is recycled to the Flash Separator 115 via line 411 as in FIG. 4. Make-up Solvent can also be added to the $C_8$-$C_{10}$ Column 409 via line 502 in order to provide additional heat transfer solvent to the flash vaporization operation. Optionally, the cut point of the $C_8$-$C_{10}$ Column 409 can be adjusted so that only $C_8$ olefins exit as overhead, along with water, via line 410. The $C_{10}$+ olefin products can then form part of the heat transfer solvent being recycled to the Flash Separator 115 via line 411.

Figure 6:
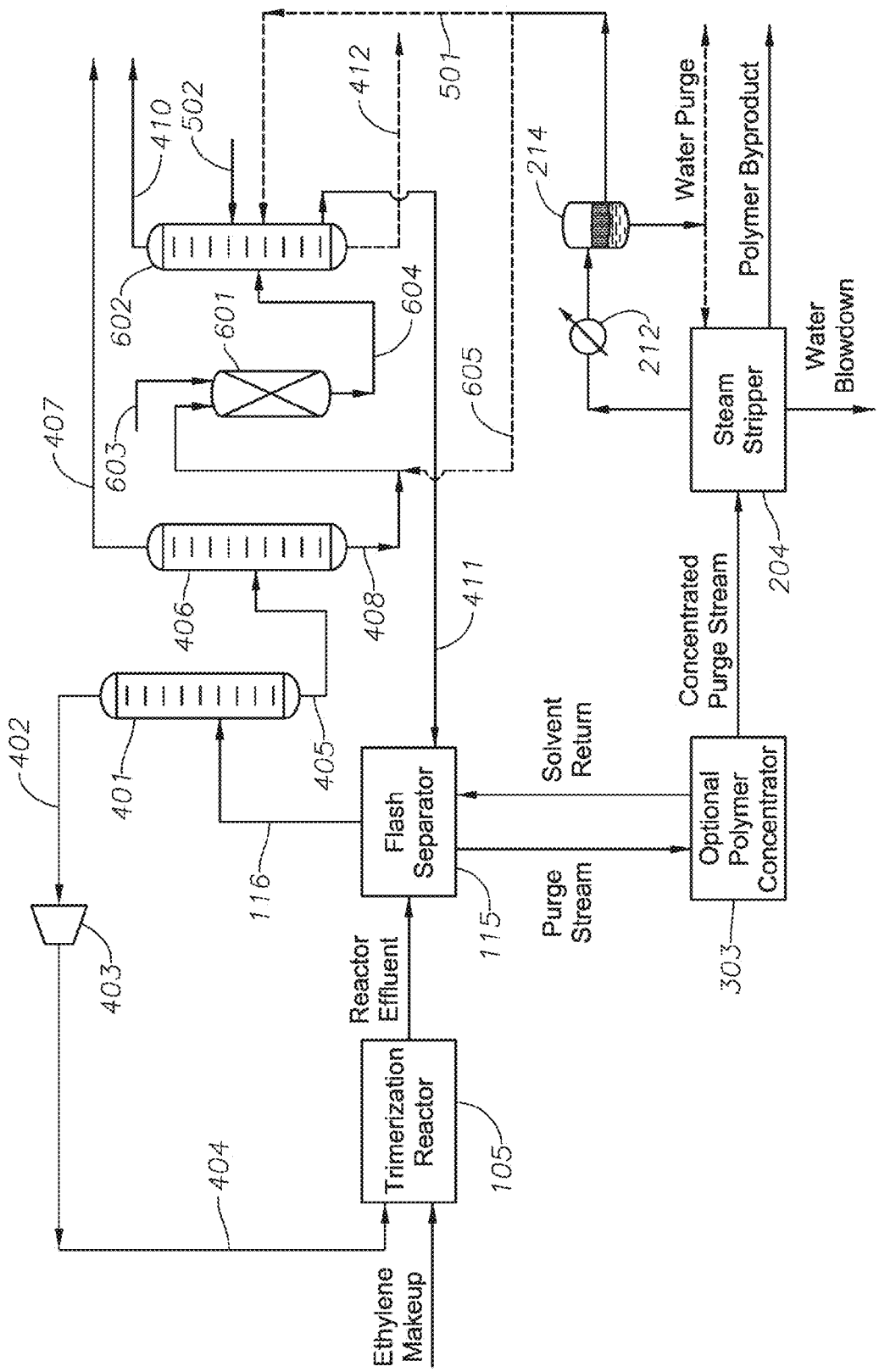
FIG. 6 illustrates one embodiment of the hydrotreating of $C_8$+ olefins recovered from the olefin oligomerization reactor effluent.

FIG. 6 of the drawings illustrates how a hydrotreating operation can be inserted into the apparatus and process configuration of FIG. 5 in order to hydrogenate the $C_8$+ olefins found in the flash vapor from the Flash Separator 115. Such hydrogenation converts all of these $C_8$+ olefins into $C_8$+ paraffins, thereby rendering them especially suitable for use in or as the heat transfer solvent.

In FIG. 6 a Hydrotreater Unit 601 is positioned to receive and hydrogenate the bottoms from the Hexene Column 406, thereby converting the $C_8$-$C_{10}$ Column 409 from FIGS. 4 and 5 into a Drying Column 602 in FIG. 6. All of the other principal elements shown in FIG. 6 remain unchanged from FIGS. 4 and 5.

In FIG. 6, hydrogen is fed to the Hydrotreater 601 via line 603 along with the bottoms from the Hexene Column 406 fed via line 408. Hydrogenated products, along with excess hydrogen, from the Hydrotreater 601 are fed to the Drying Column 602 via line 604. From the Drying Column 602, water and excess hydrogen exit as overhead via line 410. The now-saturated $C_8$+ hydrocarbons in Drying Column 602 can be removed from the bottom of the column via line 411 and fed as Solvent Recycle to the Flash Separator 115. FIG. 6 also shows that water-containing solvent recovered from the Separator 214 can be fed to the drying operation carried out in Drying Column 602 either via line 501 directly to the Drying Column 602 and/or indirectly via line 605 to the Hydrotreater 601.

Figure 7:
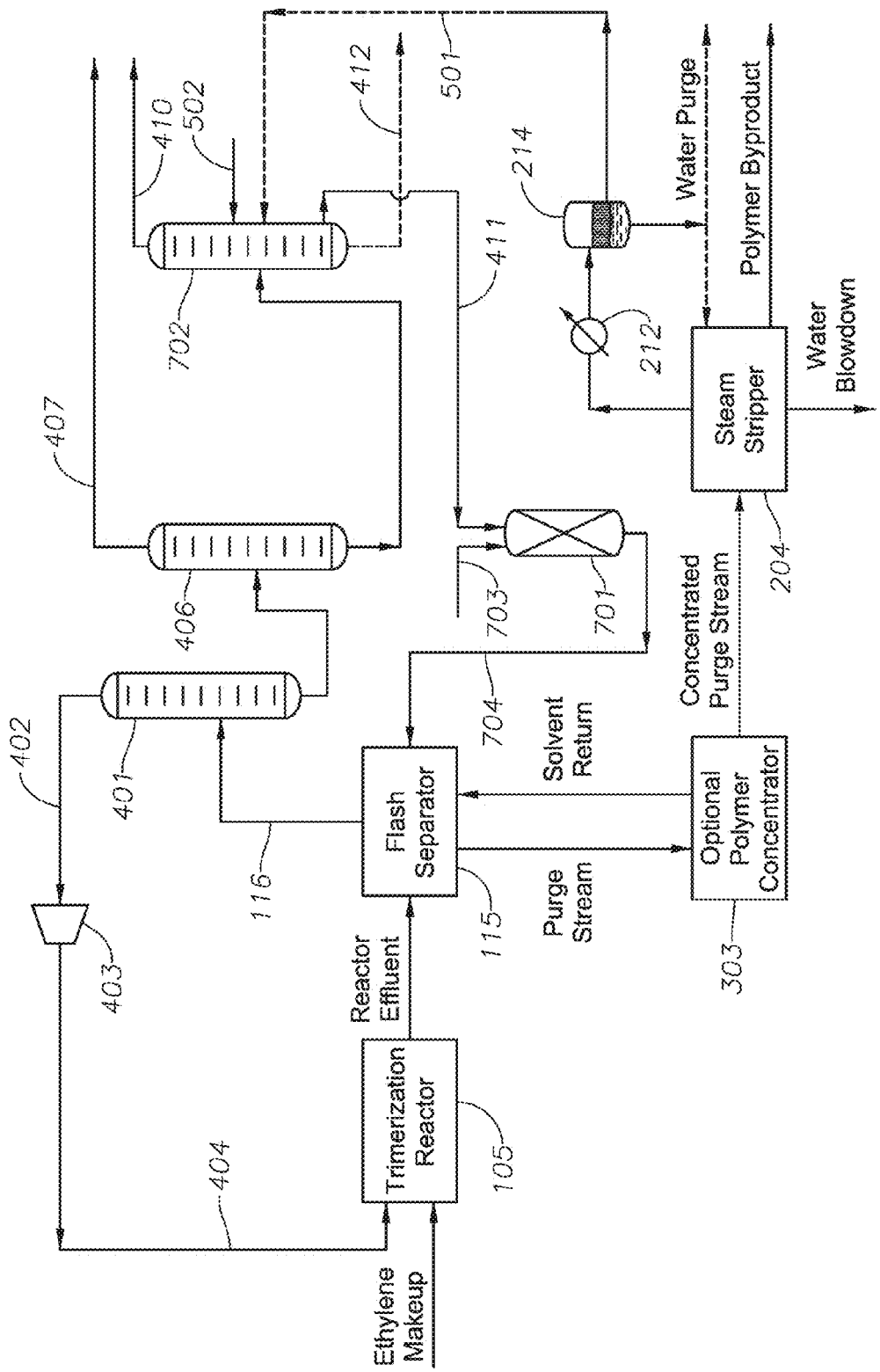
FIG. 7 illustrates a second embodiment of the hydrotreating of $C_8$+ olefins recovered from the olefin oligomerization reactor effluent.

FIG. 7 of the drawings illustrates an alternate location for a hydrotreating operation to be inserted into the apparatus and process configuration of FIG. 5 in order to hydrogenate the $C_{10}$+ olefins found in the flash vapor front the Flash Separator 115. Such hydrogenation converts all of these $C_{10}$+ olefins into $C_{10}$+ paraffins, thereby rendering them especially suitable for use in or as the heat transfer solvent. $C_8$ olefins in this FIG. 7 configuration are not hydrogenated and are recovered as olefin product.

In FIG. 7 the Hydrotreater Unit 701 is inserted to receive and hydrogenate the bottoms from what in FIG. 7 becomes a $C_8$ and Drying Column 702. All of the other principal elements shown in FIG. 7 remain unchanged from FIGS. 4 and 5.

In FIG. 7, hydrogen is fed to the Hydrotreater 701 via line 703. $C_{10}$+ olefins from the bottom of the $C_8$ and Drying Column 702 are also fed via line 411 to the Hydrotreater 701 and are hydrogenated therein to $C_{10}$+ paraffins. These hydrogenated materials from the bottom of the Hydrotreater 701 are fed via line 704 as solvent recycle to the Flash Separator 115. (With this embodiment, the Hydrotreater 701 must either (i) be operated with excess $C_{10}$+ olefin, such that a high conversion of hydrogen is achieved; or (ii) it must be acceptable to have hydrogen present in the Trimerization Reactor 105.) The $C_8$ olefin material from the flash vapor is recovered, along with water, from the overhead of the $C_8$ and Drying Column 702 via line 410.

Figure 8:
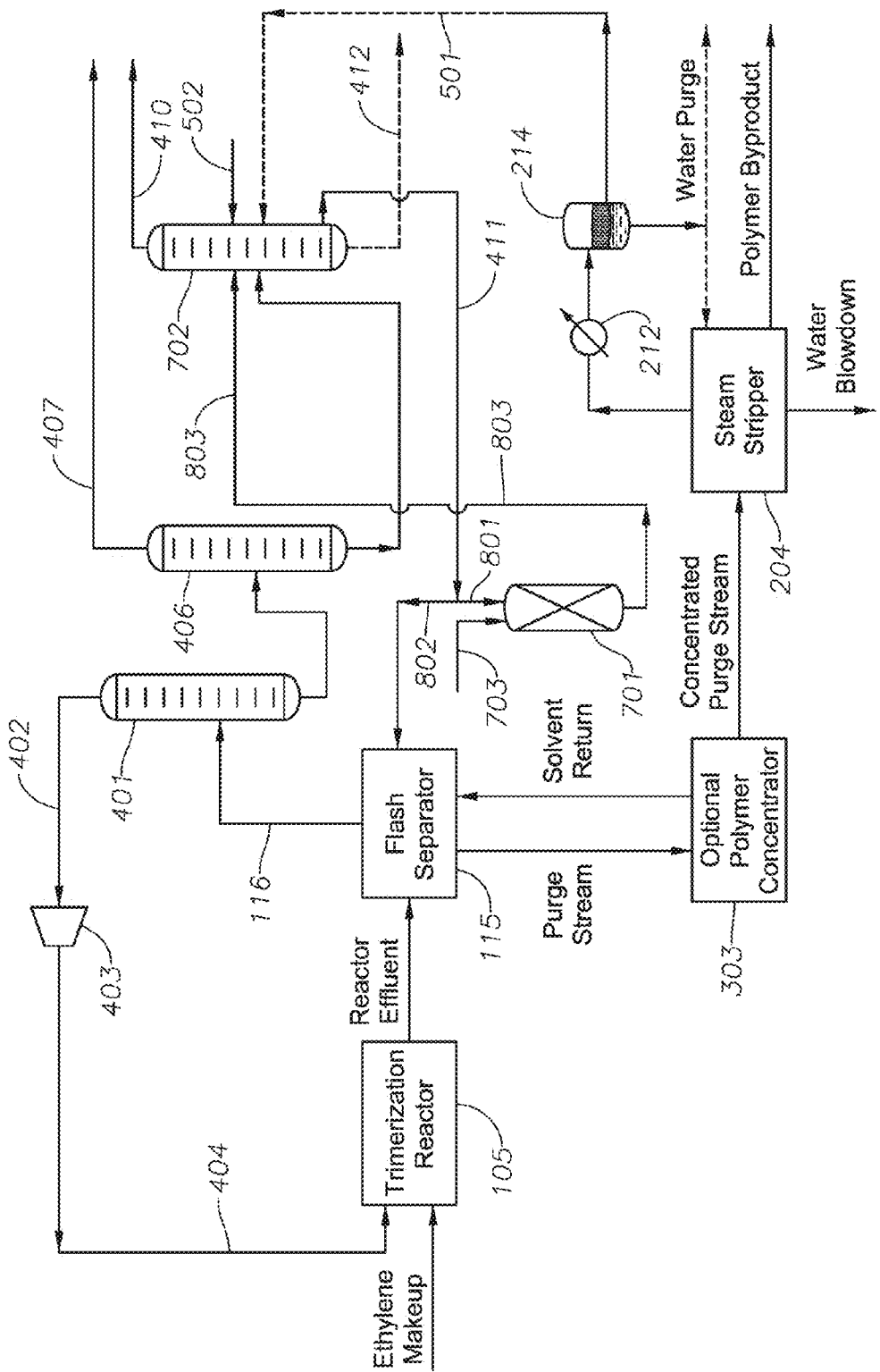
FIG. 8 illustrates a third embodiment of the hydrotreating of $C_8$+ olefins recovered from the olefin oligomerization reactor effluent.

FIG. 8 of the drawings illustrates another alternate location for a hydrotreating operation to be inserted into the apparatus and process configuration of FIG. 5 in order to hydrogenate the $C_{10}$+ olefins found in the flash vapor from the Flash Separator 115. As in the FIG. 7 configuration, such hydrogenation converts all of these $C_{10}$+ olefins into $C_{10}$+ paraffins, thereby rendering them especially suitable for use in or as the heat transfer solvent. As in FIG. 7, $C_8$ olefins in this FIG. 8 configuration are not hydrogenated and are recovered as olefin product, leaving the $C_8$ and Drying Column 702 as overhead via line 410.

In FIG. 8, the $C_{10}$+ olefins exiting via line 411 from the bottom of the $C_8$ and Drying Column 702 are split into lines 801 and 802. Line 801 feeds a portion of these materials into the Hydrotreater 701; Line 802 feeds another portion of these materials back to the Flash Separator 115 as Solvent Recycle. Hydrogenated material and excess hydrogen leave the Hydrotreater via line 803 and are fed as Solvent Recirculation to the $C_8$ and Drying Column 702. All of the other principal elements shown in FIG. 8 remain unchanged from FIG. 7.

By adjusting the proportion of the solvent stream that is recycled to the Flash Separator 115 via line 802 versus to the Hydrotreater 701 via line 801, the olefin content of the solvent system can be controlled to a desired low level. The greater the proportion of the stream (line 411) that is hydrotreated, the lower the olefin content will be in the flash vaporization solvent.

Another aspect of the present invention involving olefin oligomerization deals with the problem of build-up of polymeric by-products such as polyethylene on the surfaces of the oligomerization reactor and in the associated inet and outlet piping of the reactor. Build-up of polymeric foulant on reactor and piping internal surfaces can necessitate procedures wherein the reactor and piping must be washed with a hot solvent to remove the built-up foulant. Generally this will involve shut down of the oligomerization reactor in order to carry out the washing operation.

One technique which can be employed in connection with the olefin oligomerization operations herein to minimize build-up (and the negative effects thereof) of polymeric by-products on reactor and piping surfaces is to coat such internal surfaces with a fluorine-containing polymer. Such a fluoropolymer coating can reduce the friction is coefficient of the reactor and piping internal surfaces, thus mitigating mechanical interactions between reactor/piping surfaces and fouling particles. Fluoropolymer coating may also reduce the ability of the reactor/piping surfaces to build up charge, thereby mitigating electrostatic interactions between such surfaces and fouling particles. Finally, fluoropolymer coatings may provide a chemically inert shield around reactor internals such that chemical interactions between reactor/piping surfaces and fouling particles is minimized.

Use of a fluoropolymer coating on the internal surfaces of the oligomerization reactor(s) and associated piping can prevent polymeric by-product foulants from building up as fast as they would on untreated surfaces. The fluoropolymer coating can thus cause a smaller portion of the inevitably-produced polymeric by-products of oligomerization to stick to the reactor walls, thereby allowing a larger portion of such by-products to harmlessly flow out of the reactor with the reactor effluent. Furthermore, the polymeric foulant which does deposit on the fluoropolymer-coated surfaces is easier to remove than by-product which deposits on untreated surfaces. This aspect of the use of fluoropolymer coating makes the washing of the reactor more effective, enabling the washing solvent to clean out more of the polymeric foulant.

Fluoropolymers which can be used to coat the internal surfaces of the oligomerization reactor and piping employed in the methods, apparatus and processes herein include Fluorinated Ethylene Propylene (FEP), polytetrafluoroethylene (PTFE) and polyvinylidine fluoride (PVF). Suitable fluoropolymers for reactor coating are marketed by the 3M Company under the tradename Fluorad™.

Another embodiment of the present invention permits simultaneous olefin oligomer production and reactor washing. Unlike the methods illustrated in FIGS. 1 through 8 which employ a single oligomerization reactor, this additional embodiment carries out olefin oligomerization using a reactor system comprising a plurality of oligomerization reactors. These may be connected in series or parallel, although a series configuration is preferred to achieve better utilization of the catalyst. Then using a particular unique arrangement of four-, three- and optionally two-way valves to handle both reactor feed/effluent, also referred to herein as "reactive liquids" and wash oil for removing polymeric by-products, one of the reactors in the series can be cleaned with the wash oil while the other reactor(s) in the series can continue operating to catalytically oligomerize reactor feed introduced therein to reactor effluent containing oligomers.

As with the single reactor set-ups hereinbefore described, one or more of the oligomerization reactors and associated piping in the multiple reactor set-up can also have their interior surfaces coated with fluoropolymer material. Use of such a fluoropolymer coating can facilitate the reactor washing operations described herein in connection with the multiple reactor set-up.

The resulting oligomer-containing reactor effluent from the multiple reactor system can be treated and processed, for example, using the several effluent component separation techniques hereinbefore described such as those which utilize a heat transfer solvent to effect flash vaporization of the effluent. The same materials hereinbefore described as being useful as a heat transfer medium may also be used as the wash oil which can be pumped into the oxidation reactor(s) to be cleaned and which can remove therefrom the accumulated polymeric by-products.

As when the term "solvent" is used to describe the heat transfer medium employed in the aforementioned separation methods, the term "solvent" when applied to the reactor wash oil does not necessarily mean that the wash oil will dissolve polymeric by-product foulant in the reactor and associated piping being cleaned therewith. In some cases, the wash oil may simply serve as a heat transfer fluid to heat the polymeric by-products above their melting point, swell the polymeric matrix and entrain the polymeric by-product(s) out of the reactor/piping system.

The basic apparatus configuration of a multiple reactor system and its operation to concurrently continue olefin oligomerization while serially cleaning one reactor after another in the series of reactors in the system can be illustrated by FIGS. 9 through 14 provided herein. The apparatus elements are shown by the element letters and numbers which are carried consistently throughout FIGS. 9-14.

In each of FIGS. 9-14, there is shown a series of three interconnected oligomerization reactors designated as Reactor A, Reactor B, and Reactor C. Reactor A has to a main inlet 901 and a main outlet 902. Reactor B has a main inlet 903 and a main outlet 904. Reactor C has a main inlet 905 and a main outlet 906. Associated with main outlet 902 of Reactor A is a three-way valve 910. Associated with main outlet 904 of Reactor B is a three-way valve 911. Associated with main outlet 906 of Reactor C is a three-way valve 912.

As also shown in FIGS. 9-14, there are two four-way valves associated with each reactor in the series. Each reactor has a first four-way valve suitable for controlling liquid flow into the reactor. Thus, Reactor A has a first four-way valve 920 associated with its main inlet 901. Reactor B has first four-way valve 921 associated with its main inlet 903. Reactor C has a first four-way valve 922 associated with its main inlet 905.

Each of the reactors in the series also has a second four-way valve positioned to receive liquid flow coming from each of the three-way valves associated with each reactor main outlet. Thus in FIGS. 9-14, for Reactor A, a second four-way valve 925 is in liquid communication with three-way valve 910. For Reactor B, a second four-way valve 926 is in liquid communication with three-way valve 911. For Reactor C, a second four-way valve 927 is in liquid communication with three-way valve 912.

The second four-way valves for all but the last reactor in the series of reactors are also in liquid communication with the inlet four-way valves for the next succeeding reactors in the series. Thus in FIGS. 9-14, inlet four-way valve 921 of Reactor B is in liquid communication with outlet four-way valve 925 of Reactor A and inlet four-way valve 922 of Reactor C is in liquid communication with outlet four-way valve 926 of Reactor B.

The three-way valves associated with each reactor in the series can direct liquid coming from the reactor either to the second four-way valve associated with that reactor or via suitable outflow piping to inlet piping which can provide liquid to each reactor other than through the main reactor inlet. Thus as shown in FIGS. 9-14, outflow piping 913 from three-way valve 910, outflow piping 915 from three-way valve 911, and outflow piping 917 from three-way valve 912 can all feed liquid coming from any of the three reactors into inlet piping 919. Liquid from inlet piping 919 can be fed to any of the three reactors through any of lines 914, 916 and/or 918.

FIGS. 9-14 further show Reactor Feed line 930 which provides reactor feed into the inlet four-way valve 920 of the first Reactor A in the reactor series and Reactor Effluent line 931 which carries reactor effluent away from the outlet four-way valve 927 associated with Reactor C, the last reactor in the series. Similarly. FIGS. 9-14 further show a Wash Oil Supply line 940 which is in fluid communication with all of the inlet four-way valves, 920, 921, and 922, in the series. Also shown is a Wash Oil Return line 941 which is in fluid communication with all of the outlet four-way valves, 925, 926, and 927, in the series.

The apparatus described above with respect to the system of reactors in a series can be used in a process to maintain steady state production of oligomers, e.g., 1-hexene, with cyclic cleaning operations. In such a process, the piping which transports reactive liquid in or out of each reactor is, as shown, fitted with a four-way valve. In one position, the four-way valve directs the flow of reactive liquids into and out of the reactor when it is in the "production" mode. When rotated 90°, the four-way valve can then direct wash solvent through the reactor, including the piping which had previously contained the reactive liquids.

Just before a reactor in the series is to be washed, the reactive liquid in that reactor is transferred to the reactor which was just washed. Ethylene pressure can be used to transfer the liquid from one reactor to the other, generally via the outflow and inlet piping shown as elements 913 to 919 in FIGS. 9-14. In this manner the reactive components are "reused", thereby avoiding disposal issues with the reactive liquid (which can contain active aluminum and chromium metals that are pyrophoric.) In addition, the just-cleaned reactor can be quickly inventoried with liquid of the proper composition for a smooth transition when put back on line. The spent wash oil, i.e., solvent, used for cleaning a reactor can be sent to the flash separator hereinbefore secribed. This wash oil solvent can thus serve as solvent make-up to the hot solvent flash system, thereby effectively dealing with the polymeric foulant therein which was washed from the reactor by the solvent.

FIGS. 9-14 illustrate in a 3-reactor system the steps involved to cycle reactors through the process herein of on-line production and wash sequences. In FIGS. 9-14, liquid flow of both reactor feed/effluent and wash oil supply/return is shown by the heavy lines with arrows. Further in these FIGS. 9-14, Reactor feed/effluent (reactive liquids) within the reactors is shown by hatching. Wash oil within a reactor is shown by cross-hatching.

Figure 9:
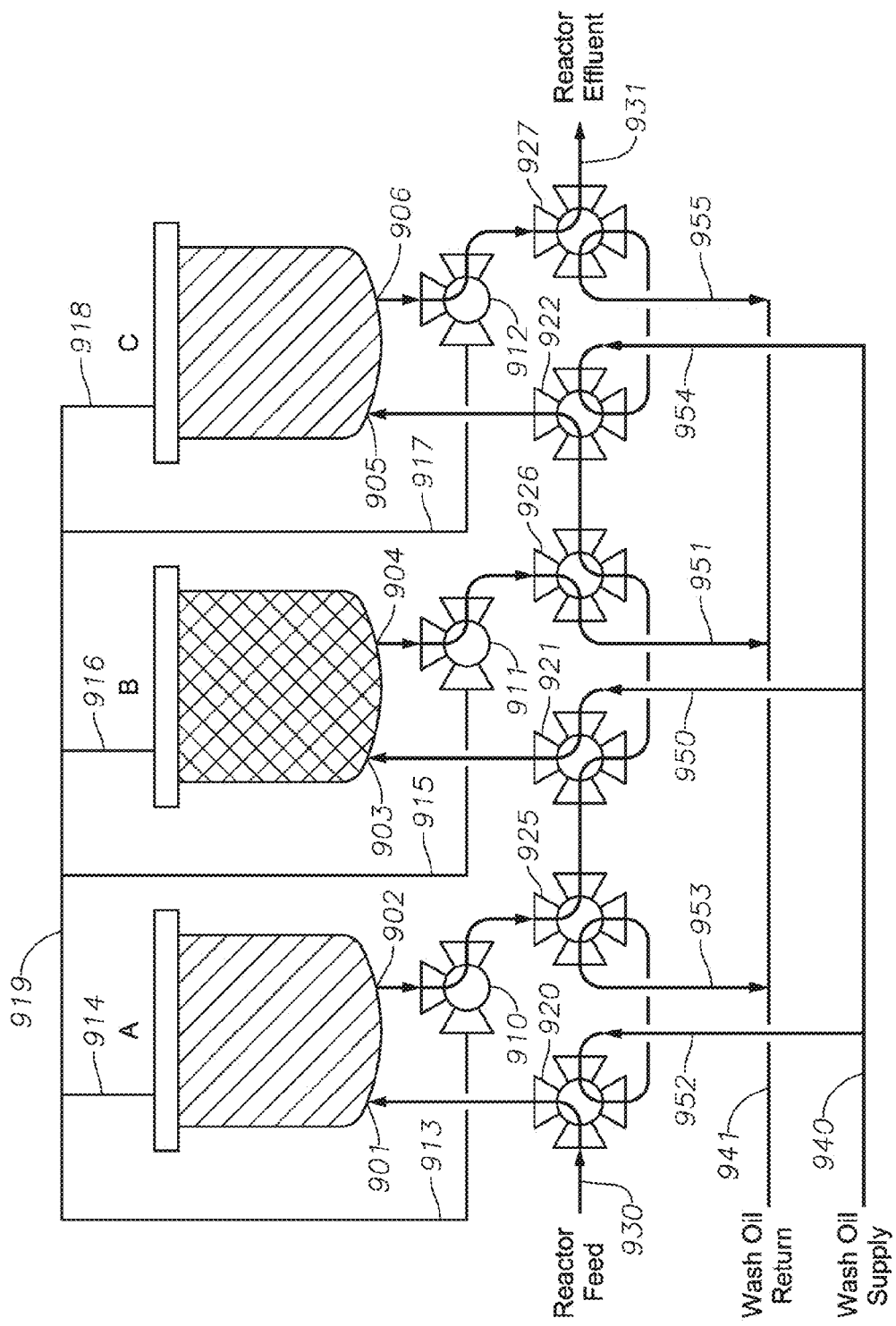
FIG. 9 illustrates a multiple reactor set-up and an initial stage in a process for using that reactor set-up to wash one reactor while using the other reactors to continue oligomerization of olefins.

In FIG. 9, Reactors A and C are on-line, and Reactor B is being washed. It can be seen from the heavy flow lines that the three- and four-way valves are set such that wash oil flows in and out of Reactor B through lines 950 and 951, respectively. For Reactors A and C, the valves are set so that wash oil by-passes those reactors by flowing through lines 952 and 953 (Reactor A) and 954 and 955 (Reactor C), respectively. It can also be seen that the valves are switched so that effluent from Reactor A by-passes Reactor B which is being washed and flows instead into Reactor C.

Figure 10:
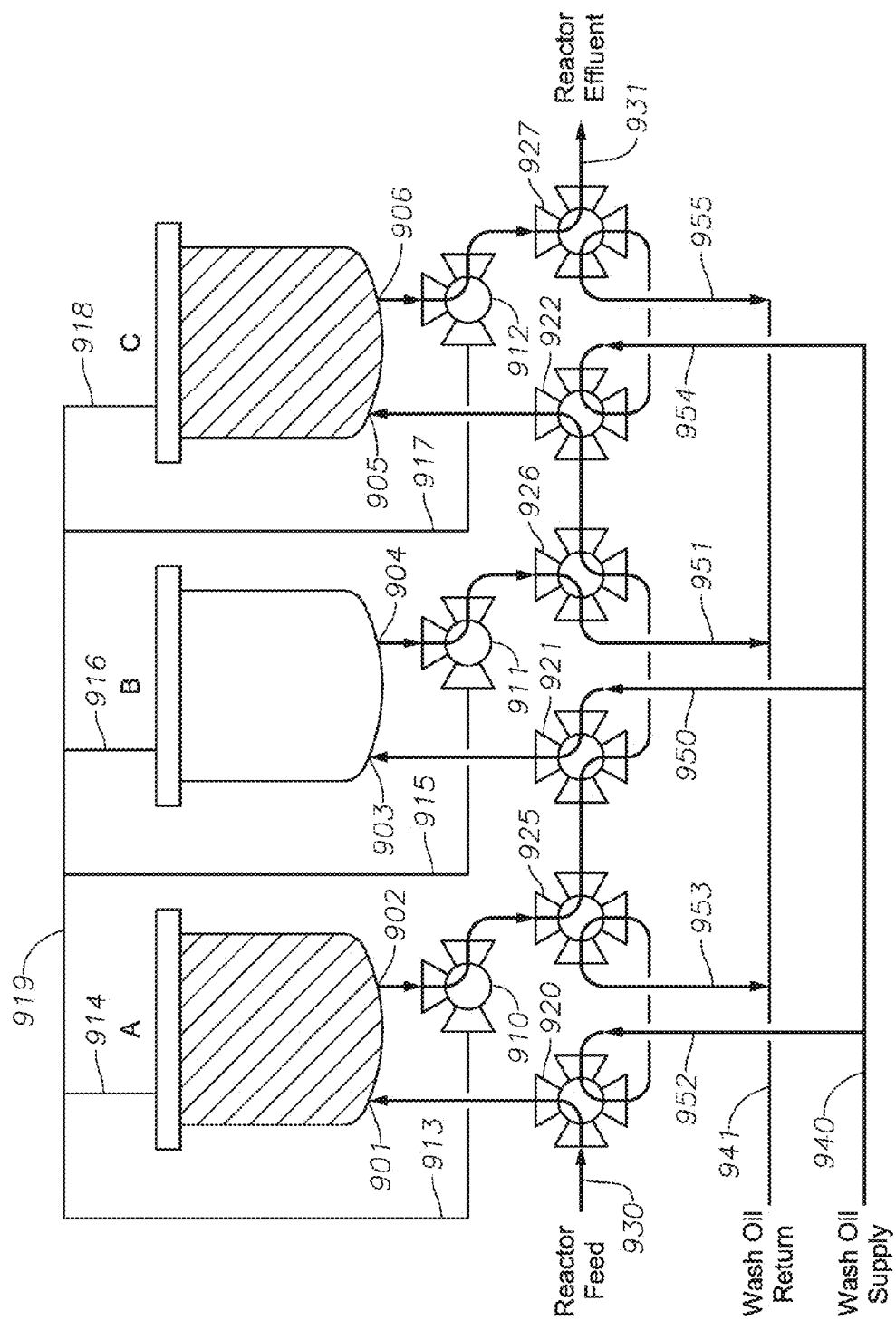
FIG. 10 illustrates a further stage in a process for using the FIG. 9 reactor set-up to drain wash solvent from the one reactor while using the other reactors to continue oligomerization of olefins.

Further progress in the process herein is shown in FIG. 10. In FIG. 10, Reactor B has completed its wash cycle and has been drained of hot solvent by means of line 951. No solvent flows into Reactor B since line 950 is closed via a two-way valve (not shown).

Figure 11:
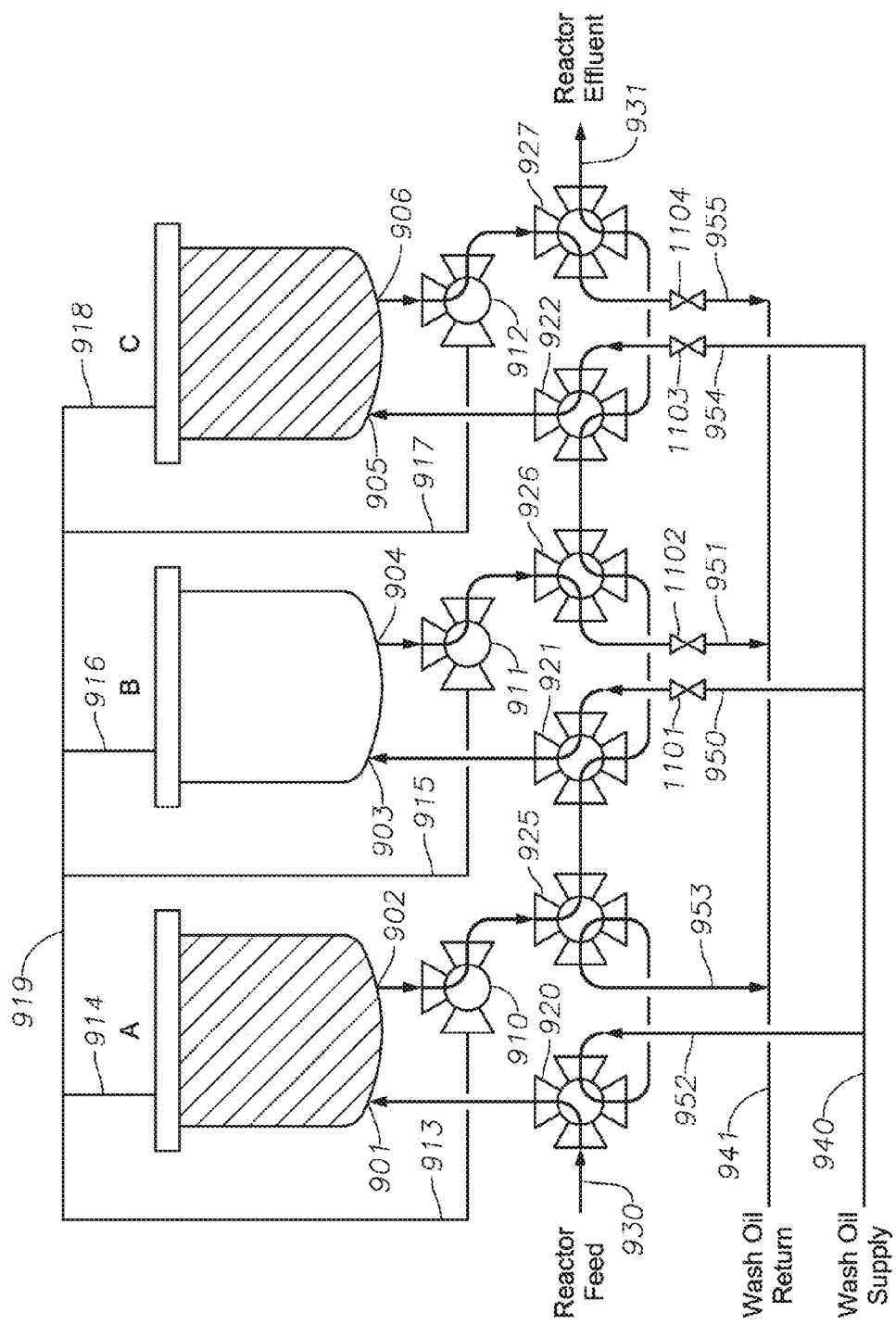
FIG. 11 illustrates yet a further stage in a process for using the FIG. 9 reactor set-up to isolate a second reactor from production while using the first reactor to continue oligomerization of olefins.

Further progress in the process herein is shown in FIG. 11. In FIG. 11, the valves are again switched so that reaction fluid is by-passed around Reactor C. At this point, the hot solvent wash system is isolated from Reactors B and C by two-way valves, 1101, 1102, 1103, and 1104, shown in the wash oil inlet and outlet lines 950, 951, 954, and 955.

Figure 12:
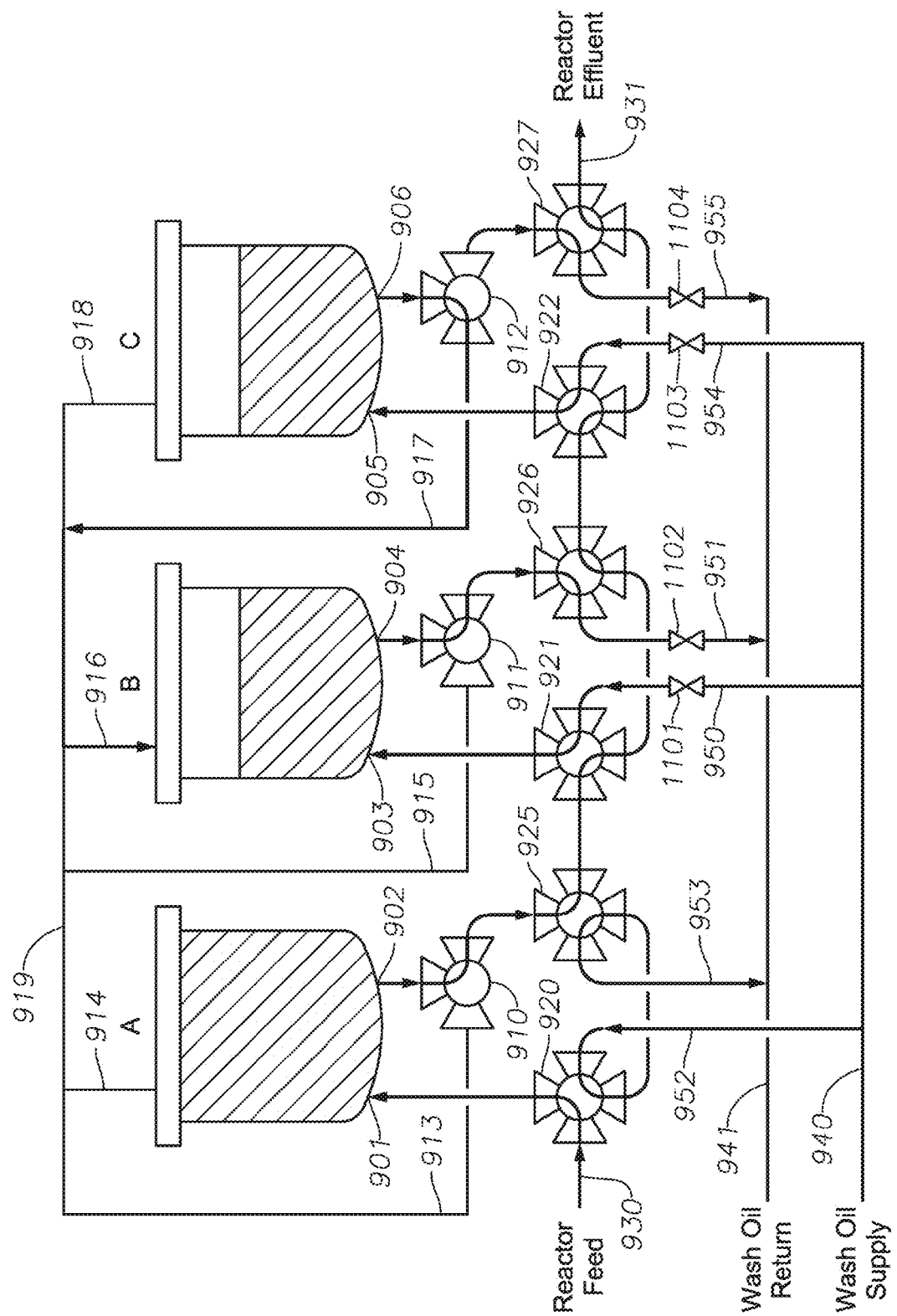
FIG. 12 illustrates yet a further stage in a process for using the FIG. 9 reactor set-up to transfer reactive fluids from the isolated second reactor to the already washed reactor while using the a first reactor to continue oligomerization of olefins.

Further progress in the process is next shown in FIG. 12. In FIG. 12, valves 1102 and 1104 are closed, and three-way valve 912 under Reactor C is rotated to transfer the reactive liquid from Reactor C to Reactor B as shown by the heavy flow line through lines 917, 919, and 916. Ethylene pressure (not shown) is used to push this liquid from Reactor C to Reactor B.

Figure 13:
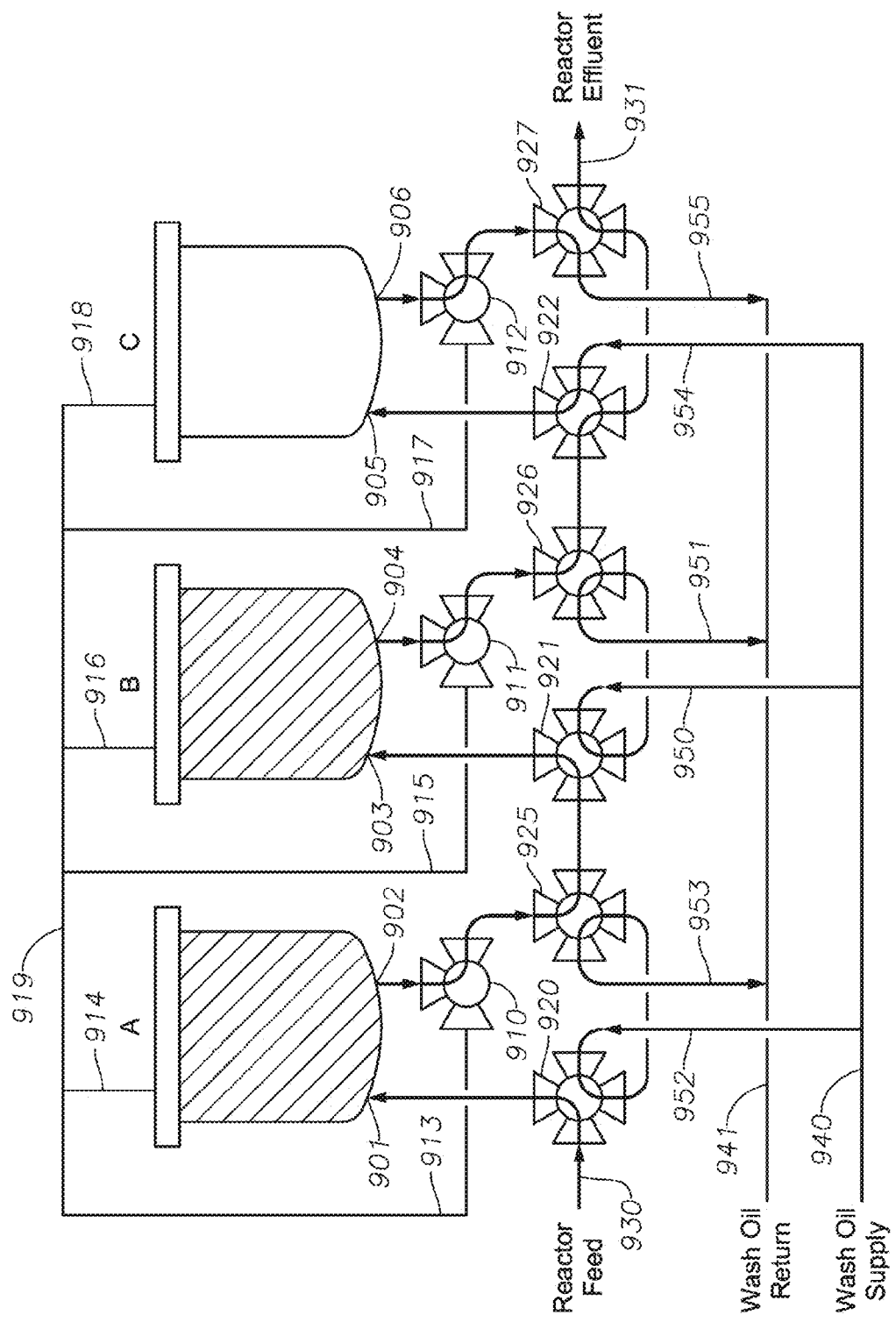
FIG. 13 illustrates yet a further stage in a process for using the FIG. 9 reactor set-up to prepare the emptied second reactor for washing while using the other reactors to continue oligomerization of olefins.

Further progress in the process is next shown in FIG. 13. In FIG. 13, all valves are switched to place Reactor B on-line and to line up the just-emptied Reactor C to the wash oil supply and return system.

Figure 14:
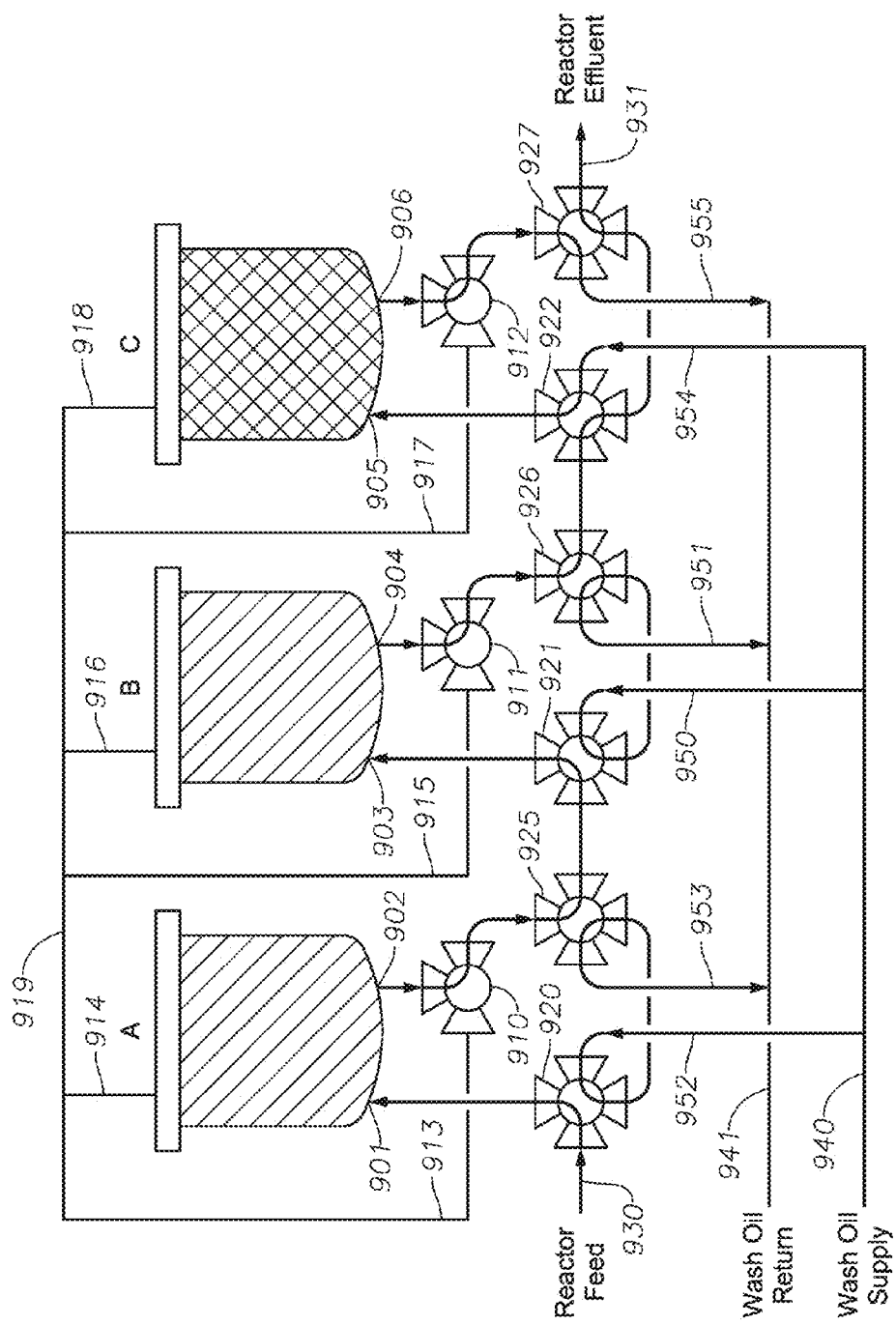
FIG. 14 illustrates yet a further stage in a process for using the FIG. 9 reactor set-up to wash the second reactor while using the other two reactors to continue oligomerization of olefins.

Further progress in the process is next shown in FIG. 14. In FIG. 14, Reactor C is shown as being filled with wash solvent and is now in the wash cycle. Meanwhile Reactors A and B continue to produce reactor effluent in series. Upon completion of washing Reactor C, Reactor C is emptied, and Reactor A would be washed next following the same steps as hereinbefore described for moving from Reactor B to C.

A specific embodiment of the principal oligomerization reactor effluent component separation method is illustrated by the following Example:

EXAMPLE 1

Using the apparatus and process flow configuration of FIG. 1, ethylene is converted to 1-hexene using isopentane as a reaction diluent and Isopar G as the recirculating heat transfer solvent. The catalyst system employed is a chromium-based catalyst with a modified methyl alumoxane activator. Run conditions for this example are set forth in Table 1.

TABLE 1

| Run Conditions - Ethylene to 1-Hexene | |
|---|---|
| Reactor Temperature (° F.)/(° C.) | 150/66 |
| Reactor Pressure (psig)/(kPa) | 230/1586 |
| Diluent Flow (lb/hr)/(kg/hr) | 4.5/4.5 |
| Residence Time (hr) | 2 |
| Run Duration (hr) | 11 |
| Catalyst Concentration (mol/gal)/(mol/l) | $1.4 \times 10^{-5}/3.70 \times 10^{-4}$ |
| Fraction 1-Hexene in Reactor Effluent (lb/lb)/(kg/kg) | 0.25/0.25 |
| Flash Separator Temperature (° F.)/(° C.) | 305/152 |
| Heater Temperature (° F.)/(° C.) | 340/171 |
| Flash Separator Pressure (psig)/(kPa) | 80/552 |
| Average Collection Rate of Flash Vapor (lb/hr)/(kg/hr) | 7.5/3.4 |
| Fraction Polyethylene in Flash Vapor (lb/lb)/(kg/kg) | 0/0 |
| Fraction 1-Hexene in Flash Vapor (lb/lb)/(kg/kg) | 0.22/0.22 |

It should be noted that the duration of this run and the volume of diluent passing into the flash separator as set forth in Table 1 would be expected to be sufficient to overfill the flash separator vessel. However, there is no increase in the liquid level in the separator inasmuch as volatile components evaporate at a rate sufficient, to avoid any liquid accumulation. In fact, there is a slow decrease in liquid level as some of the Isopar G solvent is carried out with the vapor phase. Moreover, there is no observed polymer in the condensed flash separator vapor. These two observations illustrate the ability of the method herein to achieve a steady state in which reactor products are completely separated from the unwanted polymer by-products.

Although the high temperature in the flash separator vessel serves to deactivate the catalyst, it is possible that the stated Table 1 conditions could lead one to expect some isomeration of the 1-hexene product to 2- and 3-hexene. These other isomers can have detrimental effects in processes that utilize 1-hexene, and therefore the level of other hexene isomers relative to the pure 1-hexene should be kept low. The data in the following Table show that very little of such unwanted isomerization takes place during a typical run of the flash separator system under the conditions set forth in Table 1.

TABLE 2

| Fraction of Non 1-Hexene Isomers Relative to Pure 1-Hexene | | |
|---|---|---|
| 5 Hours Into Run | Reactor Effluent (lb/lb) | 0.0000 |
|  | Flash Vapor (lb/lb) | 0.0049 |
| 9 Hours Into Run | Reactor Effluent (lb/lb) | 0.0000 |
|  | Flash Vapor (lb/lb) | 0.0027 |

Various embodiments of the invention include but are not limited to:

Embodiment 1. A process for oligomerizing ethylene to alpha-olefin product, said process comprising:
  A) oligomerizing ethylene in a diluent using a catalyst to produce a liquid reactor effluent comprising alpha-olefin product, polymeric by-products, catalyst material, and reaction diluents;
  B) contacting said reactor effluent with a solvent at pressure and temperature conditions suitable to vaporize a major portion of said alpha-olefin product but not suitable to vaporize a major portion of said polymeric by-products and said catalyst material to form a combined solvent effluent;

C) separating said combined solvent effluent into a vapor phase comprising a major portion of said alpha-olefin product and a liquid phase comprising a major portion of said polymeric by-products and said catalyst material and a major portion of said solvent;

D) recirculating a first portion of said liquid phase and contacting the reactor in effluent as set forth in Step B; and E) purging a second portion of said liquid phase in order to remove polymeric by-products and catalyst from said process.

Embodiment 2. The process of embodiment 1, wherein the alpha-olefin product is 1-hexene.

Embodiment 3. The process of embodiment 1 or 2, wherein the catalyst is an organometallic catalyst system.

Embodiment 4. The process of any on of the preceding embodiments, wherein the reactor effluent further comprises unreacted ethylene in step A.

Embodiment 5. The process any on of the preceding embodiments, wherein a major portion of said unreacted ethylene is vaporized in step B.

Embodiment 6. The process of embodiment 5, wherein said vapor phase in step C further comprises a major portion of said unreacted ethylene.

Embodiment 7. The process of embodiment 6, wherein said vaporized unreacted ethylene is separately recovered in step D.

Embodiment 8. A process for oligomerizing ethylene to alpha-olefin product, said process comprising:

A) oligomerizing ethylene in a diluent using a catalyst to produce a reactor effluent comprising alpha-olefin product, polymeric by-products, catalyst material, and reaction diluents;

B) contacting said reactor effluent with a solvent at pressure and temperature conditions suitable to vaporize a major portion of said alpha-olefin product but not suitable to vaporize a major portion of said polymeric by-products and said catalyst material to form a combined solvent-effluent;

C) separating said solvent effluent into a vapor phase comprising a major portion of said alpha-olefin product and a liquid phase comprising a major portion of said polymeric by-products and said catalyst material and a major portion of said solvent;

D) contacting a fraction of said liquid phase with steam under conditions of temperature and pressure suitable to deactivate/passivate catalyst, solidify polymeric by-products, and at least partially volatilize diluent anti/or solvent in said fraction; and E) separating and separately recovering deactivated catalyst and polymeric by-products in a liquid stream and volatilized diluent and/or heat transfer solvent in a vapor stream.

Embodiment 9. The process of embodiment 8, wherein the alpha-olefin product is 1-hexene.

Embodiment 10. The process of embodiment 8 or 9, wherein the catalyst is an organometallic catalyst system.

Embodiment 11. The process of any one of embodiments 8-10, wherein the reactor effluent further comprises unreacted ethylene in step A.

Embodiment 12. The process of embodiment 11, wherein a major portion of said unreacted ethylene is vaporized in step B.

Embodiment 13. The process of embodiment 12, wherein said vapor phase in step C further comprises a major portion of said unreacted ethylene.

Embodiment 14. A multiple reactor system for continuous oligomerization of ethylene to alpha-olefin product, said system comprising:

A) a series of at least three reactors capable of liquid communication with each other, each having an inlet and an outlet;

B) a three-way outlet valve associated with the outlet of each reactor;

C) a four-way outlet valve associated with the outlet of each reactor, located downstream of each three-way valve;

D) a four-way inlet valve associated with the inlet of each reactor;

E) a wash oil supply line;

F) a wash oil return line;

G) a reactor feed line;

H) a reactor effluent line;

I) a purge line;

J) outlet piping from each reactor connected with said three-way outlet valve and said four-way outlet valve associated with each reactor, in a manner to permit flow from each reactor independently and alternatively to:
  i) the reactor effluent line;
  ii) the wash oil return line; or
  iii) the purge line; and K) inlet piping to each reactor connected with said four-way inlet valve and said foul-way outlet valve associated with each reactor, in a manner to permit flow into each reactor independently and alternatively from:
  i) the reactor feed line;
  ii) the wash oil supply line; or
  iii) the purge line.

Embodiment 15. The reactor system of embodiment 14 wherein the interior surfaces of a major portion of one or more of the reactors, the piping, the valves, and the lines are coated with a fluorine-containing polymer.

Embodiment 16. A process for oligomerizing ethylene to alpha-olefin product in at least three reactors, said process comprising:

A) oligomerizing ethylene to alpha-olefin product in all reactors;

B) oligomerizing ethylene to alpha-olefin product in at least one reactor while oil-washing at least one reactor;

C) oligomerizing ethylene to alpha-olefin product in at least one reactor while reaction fluid from a second reactor is transferred to a third reactor;

wherein said process is operated in only one of configuration A, B, or C at a single point in time and at least in both configurations B and C over an extended period of time.

Embodiment 17. A method for separating catalyst, unreacted ethylene, and polymeric by-products from 1-hexene in a reactor effluent from a continuous process for selectively trimerizing ethylene to 1-hexene, which method comprises:

A) in a reactor, selectively trimerizing ethylene in a reaction diluent using a homogeneous organometallic catalyst system to produce a pressurized, liquid reactor effluent comprising 1-hexene reaction product, unreacted ethylene, polymeric by-products, catalyst material, reaction diluents and optionally $C_8+$ olefins;

B) reducing the pressure of said liquid reactor effluent to provide reduced pressure liquid reactor effluent;

C) contacting said reduced pressure effluent with a heated heat transfer solvent under conditions of temperature, pressure and flow rate which are effective to subsequently flash vaporize substantially all of said 1-hexene reaction product and said unreacted ethylene, but which conditions are not effective to subsequently vaporize any major portion of said polymeric by-products and said catalyst material;

D) separating said reduced pressure effluent in a flash separator into a vapor phase comprising substantially all of said 1-hexene reaction product and said unreacted ethylene, along with some reaction diluent and a minor portion of said heat transfer solvent; and a liquid phase comprising substantially all of said polymeric by-products and said catalyst material, along with some reaction diluent and a major portion of said heat transfer solvent;

E) subjecting said vapor phase from said flash separator to one or more distillation steps sufficient to recover 1-hexene, unreacted ethylene, reaction diluents, heat transfer solvent and optionally $C_8+$ olefins;

F) recirculating a first portion of said heat transfer solvent-containing liquid phase from said separator through a heater and then into contact with said reduced pressure liquid reactor effluent as set forth in Step C; and G) continuously or intermittently forming as a purge stream a second portion of said liquid phase from said separator in order to remove polymeric by-products and catalyst material from the flash separator and the recirculating first portion of said liquid phase and to prevent buildup therein of said polymeric by-products and catalyst material.

Embodiment 18. The method according to embodiment 17, wherein the organometallic catalyst system comprises a single site chromium catalyst system.

Embodiment 19. The method according to embodiment 17 or 18, wherein the single site chromium catalyst system comprises a chromium source in combination with a heterocyclic, di-aryl or phosphorus compound, along with an alkyl aluminum activator.

Embodiment 20. The method according to any one of embodiments 17-19, wherein the reaction diluent used has a boiling point of from about 50° C. to 120° C. and is selected from $C_3$-$C_6$ normal and iso-paraffins, cycloparaffins and aromatic compounds.

Embodiment 21. The method according to any one of embodiments 17-20, wherein said trimerization reaction is carried out in said reactor under temperature conditions ranging from about 25° C. to 100° C. and pressure conditions ranging from about 0 psig (0 kPa) to 1200 psig (8274 kPa).

Embodiment 22. The method according to any one of embodiments 17-21, wherein the pressure of the reactor effluent is reduced to a pressure within the range of from about 0 psig (0 kPa) to 200 psig (1379 kPa) prior to contact of said effluent with recirculating heat transfer solvent.

Embodiment 23. The method according to any one of embodiments 17-22, wherein said heat transfer solvent has a boiling point of from about 100° C. to 220° C. and is selected from $C_8+$ normal and iso-paraffins, $C_7+$ cycloparaffins, and $C_6+$ aromatic compounds.

Embodiment 24. The method according to embodiment 17, wherein said heat transfer solvent has a boiling point which is at least 50° C. higher than the boiling point of the reaction diluent.

Embodiment 25. The method according to any one of embodiments 17-24, wherein said recirculating heat transfer solvent is heated in the heater to a temperature of from about 100° C. to 300° C. prior to contact with said reactor effluent.

Embodiment 26. The method according to any one of embodiments 17-25, wherein the temperature in said flash separator ranges from about 100° C. to 200° C., and the pressure within said flash separator ranges from about 0 psig (0 kPa) to 200 psig (1379 kPa).

Embodiment 27. The method according to any one of embodiments 17-26, wherein the ratio of the flow rate of the reactor effluent to the flow rate of the recirculating heat transfer solvent is sufficient to provide a temperature difference between the temperature of the heated recirculating solvent before contact with reactor effluent and the temperature of the combined solvent/effluent stream of from about 13° C. to 17° C.

Embodiment 28. The method according to any one of embodiments 17-27, wherein heat transfer solvent comprises normal and iso paraffins which have been prepared by hydrotreating $C_8+$ olefins which have been produced as a by-product of said catalytic trimerization of ethylene to 1-hexene.

Embodiment 29. A method for passivating catalyst metals in, and recovering passivated catalyst metals, polymeric by-products, reaction diluent and heat transfer solvent from, a portion of a treated effluent stream from a reactor for the catalytic trimerization of ethylene to 1-hexene, which method comprises:

A) providing a liquid portion of a treated reactor effluent stream, which liquid portion comprises organometallic catalyst material, polymeric reaction by-products, reaction diluent, and heat transfer solvent;

B) feeding a fraction of said liquid portion as a purge stream to a steam-stripping vessel containing liquid water;

C) introducing steam, and optionally also additional liquid water, into said stripping vessel, along with said purge stream, under conditions of temperature and pressure which are effective to deactivate/passivate said purge stream catalyst material, to solidify said purge stream polymeric reaction by-product material into removable particles, and to at least partially volatilize said purge stream reaction diluent and/or heat transfer solvent;

D) removing said deactivated catalyst material and said polymeric by-product particles from said steam stripping vessel via one or more liquid streams, while also removing volatilized diluent and heat transfer solvent from said steam stripping vessel via an overhead vapor stream formed by venting of steam from said stripping vessel;

E) recovering said deactivated catalyst material and said polymeric by-product particles by separating said material and particles from said one or more liquid streams from the stripping vessel; and F) recovering said volatilized reaction diluent heat transfer solvent from said overhead vapor stream from the stripping vessel.

Embodiment 30. The method according to embodiment 29, wherein the organometallic catalyst material comprises a chromium source in combination with a heterocyclic, di-aryl or phosphorus compound, along with an alkyl aluminum activator.

Embodiment 31. The method according to embodiment 29 or 30, wherein said reaction diluent has a boiling point of from about 50° C. to 120° C. and is selected from $C_3$-$C_6$ normal and iso-paraffins, cycloparaffins and aromatic compounds, wherein said heat transfer solvent has a boiling point of from about 100° C. to 220° C. and is selected from $C_8+$ normal and iso-paraffins, $C_7+$ cycloparaffins, and $C_6+$ aromatic compounds and wherein said heat transfer solvent has a boiling point which is at least 50° C. higher than the boiling point of said reaction diluent.

Embodiment 32. The method according to any one of embodiments 29-31 which includes an additional step of cooling said liquid portion of the treated reactor effluent stream in order to concentrate the amount of catalyst material therein before feeding the resulting concentrated liquid portion to said steam stripping vessel.

Embodiment 33. The method according to any one of embodiments 29-32, wherein the temperature in the steam stripping vessel used in Step C ranges from 100° C. to 110° C., and the pressure in said steam stripping vessel is maintained at about atmospheric or slightly above atmospheric.

Embodiment 34. A multiple reactor system suitable for continuously effecting catalytic trimerization of ethylene to produce 1-hexene in at least one reactor within said system while simultaneously washing another reactor within said system, said system comprising:
- A) a series of at least three ethylene trimerization reactors in liquid communication with each other, each reactor in said series comprising a main inlet opening and associated piping to permit liquid inflow into said reactor and a main outlet opening and associated piping to permit liquid outflow from said reactor;
- B) a three-way valve associated with the main outlet piping of each reactor, each of said outlet three-way valves allowing either liquid flow away from said series of reactors for further processing or liquid flow into one or more of the other reactors in said series either as feed through said reactor main inlet or through openings other than said main inlet opening;
- C) two four-way valves associated with each reactor in said series, the first of these two four-way valves being an inlet four-way valve controlling liquid flow into said each reactor via the reactor main inlet opening and the second of these two four-way valves being an outlet four-way valve in liquid communication with the liquid coming from the outlet three-way valve of said each reactor, said second four way valve further controlling liquid flow out of said each reactor, with all of said four-way valves also being in liquid communication with each other;
- D) outflow piping from each of the three-way valves associated with each reactor in said series, which outflow piping is suitable for directing liquid flow out of each reactor to inlet piping which can transfer liquid into any of the reactors in said series via other than through the main inlet opening;
- E) a reactor feed line in liquid communication with the inlet four-way valve of the first reactor in said series of reactors and a reactor effluent line in liquid communication with the four-way valve which controls liquid flow out of the last reactor in said series of reactors; and
- F) a wash oil feed line in liquid communication via two-way valves with the inlet four-way valves of each reactor in said series of reactors and a wash oil return line in liquid communication via two-way valves with the outlet four-way valves of each reactor in said series.

Embodiment 35. The multiple reactor system according to embodiment 34, wherein at least one of the multiple reactors and/or piping associated with one or more of said reactors have the interior surfaces thereof coated with a fluorine-containing polymer.

Embodiment 36. A process for utilizing a multiple reactor system for effecting catalytic trimerization of ethylene to continuously produce 1-hexene in at least one reactor, while simultaneously washing another reactor within said system, said process comprising:

- A) continuously oligomerizing ethylene to 1-hexene in a series of at least three ethylene trimerization reactors, each reactor in said series having a main inlet with liquid flow therethrough controlled by a four-way valve and a main outlet having liquid flow therethrough controlled initially by a three-way valve and thereafter by a four-way valve, with all of said reactor valves set to permit flow of reactor feed into the first reactor in said series, to have reactor effluent from the first and each succeeding intermediate reactor in said series introduced as feed into the next succeeding reactor in said series and to permit effluent from the last reactor in said series to be removed as 1-hexene containing product;
- B) switching said reactor valves to block feed into one of said series reactors to be washed, sending this blocked feed instead to the next succeeding reactor in said series and thereby bypassing said reactor to be washed;
- C) further switching said reactor valves to permit introduction of wash oil from a valved wash oil supply line into said reactor to be washed via its main inlet, thereby effecting the washing of said reactor, and to thereafter permit removal of said wash oil from the now-washed reactor in order to empty said reactor by draining wash oil out of the main outlet of the now-washed reactor and into a valved wash oil return line;
- D) further switching both the reactor valves and the wash oil line valves in order to isolate both the now-washed empty reactor and the next succeeding series reactor to be next washed from the wash oil supply and return lines and also in order to block feed into said reactor to be next washed, sending this blocked feed instead to the next succeeding reactor thereafter in said series and thereby bypassing said reactor to be next washed;
- E) switching the three-way valve at the main outlet of the next succeeding reactor to be next washed so that the reaction mixture contents thereof, prior to washing, can be and are pumped into the just-washed, and empty preceding reactor;
- F) further switching said reactor and wash oil line valves to permit introduction of wash oil from into the now-emptied reactor to be next washed via its main inlet and to thereafter permit removal of said wash oil from the now-washed next reactor by draining wash oil out of the main outlet of the now-washed next reactor and into a valved wash oil return line; and
- G) repeating Steps D, F, and F, as needed to sequentially wash and prepare for washing the next remaining reactors in said series in need of washing while continuing to trimerize ethylene to 1-hexene in the reactor(s) not being washed or prepared for washing.

Embodiment 37. The process according to embodiment 36, wherein the wash oil used in said process has a boiling point of from about 100° C. to 200° C. and is selected from $C_8+$ normal and iso-paraffins, $C_7+$ cycloparaffins, and $C_6+$ aromatic compounds.

Embodiment 38. In a process for oligomerizing ethylene to 1-olefin oligomers in a reactor vessel by introducing via reactor inlet piping ethylene, organometallic oligomerization catalyst and reaction diluents into said reactor vessel, by thereafter maintaining conditions of temperature, pressure and residence time within said reactor vessel which are effective to bring about oligomerization of said ethylene, and by removing from said reactor vessel via reactor outlet piping a reaction product effluent comprising ethylene oligomers, unreacted ethylene, oligomerization catalyst, reaction diluent and polymeric reaction by-products, the improvement which comprises carrying out said process using a reactor vessel and/or reactor inlet and outlet piping which has the interior surfaces thereof coated with a fluorine-containing polymer.

Embodiment 39. The improved process according to embodiment 38, wherein the fluorine-containing polymer used to coat the reactor vessel and piping interior surfaces is selected from fluorinated ethylene propylene (FEP), polytetrafluoroethylene (PTFE) and polyvinylidine fluoride (PVF).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for oligomerizing ethylene to alpha-olefin product, said process comprising:
   A) oligomerizing ethylene using a catalyst to produce a reactor effluent comprising alpha-olefin product, polymeric by-product, catalyst material, and reaction diluent;
   B) contacting said reactor effluent with a solvent at pressure and temperature conditions suitable to vaporize a major portion of said alpha-olefin product but not suitable to vaporize a major portion of said polymeric by-product and said catalyst material to form a combined solvent effluent;
   C) separating said combined solvent effluent into a vapor phase comprising a major portion of said alpha-olefin product and a liquid phase comprising a major portion of said polymeric by-product and said catalyst material and a major portion of said solvent;
   D) recirculating a first portion of said liquid phase to act as said solvent in contacting Step B; and
   E) purging a second portion of said liquid phase from said process.

2. The process of claim 1, wherein the alpha-olefin product is 1-hexene.

3. The process of claim 1, wherein the catalyst is an organometallic catalyst system.

4. The process of claim 1, wherein the reactor effluent further comprises unreacted ethylene in step A.

5. The process of claim 4, further comprising:
   (F) subjecting said vapor phase to one or more distillation steps sufficient to separately recover alpha-olefin product, unreacted ethylene, diluent, and solvent.

6. The process of claim 4, wherein a major portion of said unreacted ethylene is vaporized in step B.

7. The process of claim 4, wherein said vapor phase in step C further comprises a major portion of said unreacted ethylene.

8. The process of claim 4, wherein said vaporized unreacted ethylene is separately recovered in step F.

9. A method for separating catalyst, unreacted ethylene, and polymeric by-products from 1-hexene in a reactor effluent from a continuous process for selectively trimerizing ethylene to 1-hexene, which method comprises:
   A) in a reactor, selectively trimerizing ethylene in a reaction diluent using a homogeneous organometallic catalyst system to produce a pressurized, liquid reactor effluent comprising 1-hexene reaction product, unreacted ethylene, polymeric by-product, catalyst material, reaction diluent and optionally $C_8+$ olefin;
   B) reducing the pressure of said liquid reactor effluent to provide reduced pressure liquid reactor effluent;
   C) contacting said reduced pressure effluent with a heated heat transfer solvent under conditions of temperature, pressure, and flow rate which are effective to subsequently flash vaporize substantially all of said 1-hexene reaction product and said unreacted ethylene, but which conditions are not effective to subsequently vaporize any major portion of said polymeric by-product and said catalyst material;
   D) separating said reduced pressure effluent in a flash separator into a vapor phase comprising substantially all of said 1-hexene reaction product and said unreacted ethylene, along with some reaction diluent and a minor portion of said heat transfer solvent; and a liquid phase comprising substantially all of said polymeric by-products and said catalyst material, along with some reaction diluent and a major portion of said heat transfer solvent;
   E) subjecting said vapor phase from said flash separator to one or more distillation steps sufficient to recover 1-hexene, unreacted ethylene, reaction diluent, heat transfer solvent, and optionally $C_8+$ olefin;
   F) recirculating a first portion of said heat transfer solvent-containing liquid phase from said separator through a heater and then into contact with said reduced pressure liquid reactor effluent as set forth in Step C; and
   G) continuously or intermittently forming as a purge stream a second portion of said liquid phase from said separator in order to remove polymeric by-products and catalyst material from the flash separator and the recirculating first portion of said liquid phase and to prevent buildup therein of said polymeric by-products and catalyst material.

10. The method according to claim 9, wherein the organometallic catalyst system comprises a single site chromium catalyst system.

11. The method according to claim 10, wherein the single site chromium catalyst system comprises a chromium source in combination with a heterocyclic, di-aryl, or phosphorus compound, along with an alkyl aluminum activator.

12. The method according to claim 9, wherein the reaction diluent used has a boiling point of from about 50° C. to 120° C. and is selected from $C_3$-$C_6$ normal and iso-paraffins, cycloparaffins and aromatic compounds.

13. The method according to claim 9, wherein said trimerization reaction is carried out in said reactor under temperature conditions ranging from about 25° C. to 100° C. and pressure conditions ranging from about 0 psig (0 kPa) to 1200 psig (8274 kPa).

14. The method according to claim 9, wherein the pressure of the reactor effluent is reduced to a pressure within the range of from about 0 psig (0 kPa) to 200 psig (1379 kPa) prior to contact of said effluent with recirculating heat transfer solvent.

15. The method according to claim 9, wherein said heat transfer solvent has a boiling point of from about 100° C. to 220° C. and is selected from $C_8+$ normal and iso-paraffins, $C_7+$ cycloparaffins, and $C_6+$ aromatic compounds.

16. The method according to claim 15, wherein said heat transfer solvent has a boiling point which is at least 50° C. higher than the boiling point of the reaction diluent.

17. The method according to claim 9, wherein said recirculating heat transfer solvent is heated in the heater to a temperature of from about 100° C. to 300° C. prior to contact with said reactor effluent.

18. A method for passivating catalyst metals in, and recovering passivated catalyst metals, polymeric by-products, reaction diluent and heat transfer solvent from, a portion of a treated effluent stream from a reactor for the catalytic trimerization of ethylene to 1-hexene, which method comprises:

A) providing a liquid portion of a treated reactor effluent stream, which liquid portion comprises organometallic catalyst material, polymeric reaction by-products, reaction diluent, and heat transfer solvent;

B) feeding a fraction of said liquid portion as a purge stream to a steam-stripping vessel containing liquid water;

C) introducing steam, and optionally also additional liquid water, into said stripping vessel, along with said purge stream, under conditions of temperature and pressure which are effective to deactivate/passivate said purge stream catalyst material, to solidify said purge stream polymeric reaction by-product material into removable particles, and to at least partially volatilize said purge stream reaction diluent and/or heat transfer solvent;

D) removing said deactivated catalyst material and said polymeric by-product particles from said steam stripping vessel via one or more liquid streams, while also removing volatilized diluent and heat transfer solvent from said steam stripping vessel via an overhead vapor stream formed by venting of steam from said stripping vessel;

E) recovering said deactivated catalyst material and said polymeric by-product particles by separating said material and particles from said one or more liquid streams from the stripping vessel; and F) recovering said volatilized reaction diluent and heat transfer solvent from said overhead vapor stream from the stripping vessel.

19. The method according to claim 18, wherein said reaction diluent has a boiling point of from about 50° C. to 120° C. and is selected from $C_3$-$C_6$ normal and iso-paraffins, cyclo-paraffins and aromatic compounds, wherein said heat transfer solvent has a boiling point of from about 100° C. to 220° C. and is selected from $C_8$+ normal and iso-paraffins, $C_7$+ cyclo-paraffins, and $C_6$+ aromatic compounds and wherein said heat transfer solvent has a boiling point which is at least 50° C. higher than the boiling point of said reaction diluent.

20. The method according to claim 18, wherein the temperature in the steam stripping vessel used in Step C ranges from 100° C. to 110° C., and the pressure in said steam stripping vessel is maintained at about atmospheric or slightly above atmospheric.

* * * * *